US008222274B2

(12) United States Patent
Seo et al.

(10) Patent No.: US 8,222,274 B2
(45) Date of Patent: Jul. 17, 2012

(54) PYRROLE DERIVATIVE OR SALT THEREOF

(75) Inventors: Ryushi Seo, Tokyo (JP); Hidetaka Kaku, Tokyo (JP); Hiroyoshi Yamada, Tokyo (JP); Daisuke Kaga, Tokyo (JP); Shinobu Akuzawa, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 844 days.

(21) Appl. No.: 12/278,609

(22) PCT Filed: Feb. 19, 2007

(86) PCT No.: PCT/JP2007/052943

§ 371 (c)(1),
(2), (4) Date: Aug. 7, 2008

(87) PCT Pub. No.: WO2007/097276

PCT Pub. Date: Aug. 30, 2007

(65) Prior Publication Data

US 2009/0036421 A1 Feb. 5, 2009

(30) Foreign Application Priority Data

Feb. 20, 2006 (JP) ................................ P2006-041830

(51) Int. Cl.

| | |
|---|---|
| *C07D 401/12* | (2006.01) |
| *C07D 207/327* | (2006.01) |
| *C07D 401/04* | (2006.01) |
| *C07D 403/06* | (2006.01) |
| *C07D 405/06* | (2006.01) |
| *C07D 405/04* | (2006.01) |
| *C07D 403/12* | (2006.01) |
| *C07D 409/04* | (2006.01) |
| *C07D 409/12* | (2006.01) |
| *C07D 413/04* | (2006.01) |
| *A61K 31/40* | (2006.01) |
| *A61K 31/4025* | (2006.01) |
| *A61K 31/422* | (2006.01) |
| *A61K 31/439* | (2006.01) |
| *A61K 31/454* | (2006.01) |
| *A61P 1/00* | (2006.01) |

(52) U.S. Cl. ........ 514/305; 514/326; 514/343; 514/378; 514/414; 514/422; 514/423; 546/133; 546/208; 546/279.1; 548/248; 548/468; 548/517; 548/518; 548/525; 548/527; 548/537

(58) Field of Classification Search ........................ None
See application file for complete search history.

(56) References Cited

U.S. PATENT DOCUMENTS

| | | | | |
|---|---|---|---|---|
| 3,391,157 A * | 7/1968 | Pachter et al. | ................ | 548/540 |
| 3,407,199 A * | 10/1968 | Pachter | ......................... | 544/141 |
| 3,410,857 A * | 11/1968 | Schoen et al. | ................ | 546/208 |
| 3,551,571 A * | 12/1970 | Pachter et al. | ................ | 514/422 |
| 5,629,317 A | 5/1997 | Audia et al. | | |
| 6,248,894 B1 * | 6/2001 | Phillion et al. | ................ | 548/110 |
| 6,440,988 B1 | 8/2002 | Craig | | |
| 6,534,535 B1 | 3/2003 | Zhu et al. | | |
| 2004/0167129 A1 | 8/2004 | Mayweg et al. | | |
| 2004/0171881 A1 | 9/2004 | John et al. | | |
| 2004/0235899 A1 | 11/2004 | Maria Assunta et al. | | |
| 2004/0266775 A1 * | 12/2004 | Kleemann et al. | ............ | 514/248 |
| 2005/0101657 A1 | 5/2005 | Furuya et al. | | |
| 2005/0148632 A1 | 7/2005 | Tokumasu et al. | | |
| 2005/0250769 A1 | 11/2005 | Mayweg et al. | | |
| 2006/0122230 A1 * | 6/2006 | Berggren et al. | ............. | 514/326 |
| 2007/0037974 A1 | 2/2007 | Brotherton-Pleiss et al. | | |
| 2008/0171788 A1 | 7/2008 | Akuzawa et al. | | |
| 2009/0062363 A1 | 3/2009 | Kaku et al. | | |

FOREIGN PATENT DOCUMENTS

| | | |
|---|---|---|
| AU | 68844/94 | 2/1995 |
| EP | 0 622 356 | 11/1994 |
| EP | 0 639 573 | 2/1995 |
| EP | 1 466 902 | 10/2004 |
| EP | 1 541 172 | 6/2005 |
| EP | 1 716 867 | 2/2006 |
| EP | 1 728 784 | 6/2006 |
| EP | 1 852 129 | 7/2007 |

(Continued)

OTHER PUBLICATIONS

Barbara, G. et al., "A Role for Inflammation in Irritable Bowel Syndrome?", Gut, 51: i41-i44, 2002.*
Registry No. 947489-75-0, entered Registry file in STN on Sep. 18, 2007.*
Kitano, et al., "Synthesis and Biological Activity of N-(Aminoiminomethyl)-1H-indole Carboxamide Derivatives as Na+/H+ Exchanger Inhibitors", Chem. Pharm. Bull, vol. 47, No. 11 (1999) 1538-48.
Kuroita, et al., "Design and Synthesis of 6-Chloro-3,4-dihydro-4-methyl-2H-1,4-benzoxazine-8-carboxamide Derivatives as Potent Serotonin-3 (5-HT3) Receptor Antagonist", Chem. Pharm. Bull., vol. 44, No. 4 (1996) 756-64.
Lopez-Rodriguez, et al., "Benzimidazole Derivatives. 3. 3D-QSAR/CoMFA Model and Computational Simulation for the Recognition of 5-HT4 Receptor Antagonists", J. Med. Chem., vol. 45, No. 22 (2002) 4806-15.

(Continued)

*Primary Examiner* — Fiona T Powers
(74) *Attorney, Agent, or Firm* — Fitzpatrick, Cella, Harper & Scinto

(57) ABSTRACT

[Problem] To provide a compound which may be used for the prevention and/or treatment of diseases in which 5-$HT_{2B}$ receptor and 5-$HT_7$ receptor are concerned, particularly for the treatment of irritable bowel syndrome (IBS).

[Means for Resolution] It was found that a pyrrole derivative characterized by the possession of a guanidinocarbonyl group or amido group as a substituent group at the 3-position, or a pharmaceutically acceptable salt thereof, has a strong antagonism for both of the 5-$HT_{2B}$ receptor and 5-$HT_7$ receptor. In addition, the compound of the present invention having the antagonistic activity for both of the receptors showed a good pharmacological action in comparison with the case in which an antagonist selective for either one of the receptors was used alone. Based on the above, the compound of the present invention is useful for the prevention and/or treatment of diseases in which 5-$HT_{2B}$ receptor and 5-$HT_7$ receptor are concerned, particularly for the treatment of irritable bowel syndrome (IBS).

14 Claims, 3 Drawing Sheets

FOREIGN PATENT DOCUMENTS

| | | | |
|---|---|---|---|
| EP | 1 923 387 | | 5/2008 |
| JP | 8-48671 | | 2/1996 |
| JP | 9-510216 | | 10/1997 |
| JP | 2003-252854 | | 9/2003 |
| JP | 2004-534816 | | 11/2004 |
| JP | 2005-162657 | | 6/2005 |
| JP | 2005-520791 | | 7/2005 |
| WO | 95/24200 | | 9/1995 |
| WO | 02/056010 | | 7/2002 |
| WO | 03/000252 | | 1/2003 |
| WO | 03/040096 | | 5/2003 |
| WO | 2004/014428 | | 2/2004 |
| WO | 2004/060870 | | 7/2004 |
| WO | 2005/108393 | | 11/2005 |
| WO | 2006/085510 | | 8/2006 |
| WO | WO 2007/094513 | * | 8/2007 |

OTHER PUBLICATIONS

Scalzo, et al., “Studies on Anti-Candida agents with a pyrrole moiety. Synthesis and microbiological activity of some . . . ”, Il Farmaco, vol. 47, No. 7-8 (1992) 1047-53.

Borman, et al, “Functional evidence for a 5-HT2B receptor mediating contraction of longitudinal muscle in human small intestine”, British Journal of Pharmacology, vol. 114 (1995) 1525-27.

CHEMCATS(STN); Accession No. 2006:3660611; Chemical Name: Piperazine, 1-[(2-chlorophenyl)sulfonyl]-4-[[2,5dimethyl-I-(2-thienylmethyl)-IH-pyrrol-3-yl]carbonyl]; CAS Registry No. 878918-78-6.

Bianchi, et al., “Solution Phase Synthesis of a Library of Tetrasubstituted Pyrrole Amides”, J. Comb. Chem., vol. 8, No. 4 (2006) 491-99.

Tuladhar, et al., “5-HT7 receptors mediate the inhibitory effect of 5-HT on peristalsis in the isolated guinea-pig ileum”, British Journal of Pharmacology, vol. 138 (2003) 1210-14.

Liu, et al., “Expression patterns of 5-HT7 receptor isoforms in the rat digestive tract”, Life Sciences, vol. 69 (2001) 2467-75.

Carter, et al., “Characterization of a postjunctional 5-HT receptor mediating relaxation of guinea-pig isolated ileum”, European Journal of Pharmacological, vol. 280 (1995) 243-50.

Borman, et al., “5-HT2B receptors play a key role in mediating the excitatory effects of 5-HT in human colon in vitro”, British Journal of Pharmacology, vol. 135 (2002) 1144-51.

Minetto, et al., “Microwave-Assisted Paal-Knorr Reaction—Three-Step Regiocontrolled Synthesis of Polysubstituted Furans, Pyrroles and Thiophenes”, Eur. J. Org. Chem., vol. 24 (2005) 5277-88.

DePonti, et al., “Irritable Bowel Syndrome, New Agents Targeting Serotonin Receptor Subtypes”, Drugs, vol. 61, No. 3 (2001) 317-32.

Talley,et al., “Pharmacologic Therapy for the Irritable Bowel Syndrome”, The American Journal of Gastroenterology, vol. 98, No. 4 (2003) 750-58.

Kim, et al., “Serotonin: A Mediator of the Brain-Gut Connection”, The American Journal of Gastroenterology, vol. 95, No. 10 (2000) 2698-2709.

Bearcroft, et al., “Postprandial plasma 5-hydroxytryptamine in diarrhoea predominant irritable bowel syndrome: a pilot study”, Gut, vol. 42 (1998) 42-6.

Hoyer, et al., VII. International Union of Pharmacology Classification of Receptors for 5-Hydroxytryptamine (Serotonin), Pharmacological Reviews, vol. 46, No. 2 (1994) 157-203.

Whorwell et al., “Bladder smooth muscle dysfunction in patients with irritable bowel syndrome”, Gut, vol. 27 (1986) 1014-17.

Theoharides, et al., “Interstitial cystitis: bladder pain and beyond”, Expert Opin. Pharmacother., vol. 9, No. 17 (2008) 2979-94.

Patani, et al., “Bioisosterism: A Rational Approach in Drug Design”, Chem. Rev., vol. 96 (1996) 3147-76.

* cited by examiner

PYRROLE DERIVATIVE OR SALT THEREOF

TECHNICAL FIELD

The present invention relates to a pharmaceutical, particularly a pyrrole derivative which is useful as a therapeutic agent for irritable bowel syndrome.

BACKGROUND OF THE INVENTION

Serotonin (5-HT) is a monoamine neurotransmitter and expresses various physiological actions via a 5-HT receptor. The 5-HT receptor is classified into seven families of from $5\text{-HT}_1$ to $5\text{-HT}_7$. Particularly, the $5\text{-HT}_2$ receptor is known to have three subtypes, $5\text{-HT}_{2A}$, $5\text{-HT}_{2B}$ and $5\text{-HT}_{2C}$ (Non-patent Reference 1).

The irritable bowel syndrome (IBS) is a disease in which an abdominal pain or an abdominal unpleasantness continues for a prolonged period of time. Based on its symptoms, IBS is classified into a diarrhea type, a constipation type and a mixed type of diarrhea and constipation. In each case, it has been pointed out that there is a causal relation between the morbid state and the amount of 5-HT in blood. For example, there is a reference which points out that increase of blood 5-HT concentration after meal occurs in diarrhea type IBS patients and this is deeply concerned in the morbid state (Non-patent Reference 2).

Currently, though it is at the clinical trial in Japan, a 5-HT receptor antagonist or a 5-HT receptor agonist has been used in Europe and America as a therapeutic agent for IBS. As a therapeutic agent for diarrhea type, alosetron ($5\text{-HT}_3$ receptor antagonist) is used in the clinical field, but side effects such as ischemic colitis, constipation and the like have been reported. In addition, as a therapeutic agent for constipation type, tegaserod ($5\text{-HT}_4$ receptor agonist) is used in the clinical field in Europe and America, but side effects have also been reported (Non-patent Reference 3 and 4).

In recent years, pharmacological studies on other 5-HT receptor subtypes have also been carried out (Non-patent Reference 5). Regarding the $5\text{-HT}_{2B}$ receptor and $5\text{-HT}_7$ receptor, there are reports which pointed out roles of said receptors in digestive tracts. For example, there are reports stating that the $5\text{-HT}_{2B}$ receptor localizes in human ileum longitudinal muscle and a $5\text{-HT}_{2B}$ receptor antagonistic compound suppresses contraction by 5-HT (Non-patent Reference 6), and that the $5\text{-HT}_{2B}$ receptor localizing in human colon is concerned in the 5-HT-induced contraction at the time of electric stimulation and a $5\text{-HT}_{2B}$ receptor antagonistic compound suppresses it (Non-patent Reference 7).

In addition, there are reports stating that the $5\text{-HT}_7$ receptor localizes in guinea pig small intestines (Non-patent Reference 8) and rat small intestines (Non-patent Reference 9) and is concerned in the peristalsis of guinea pig ileum (Non-patent Reference 10).

Also, in the Patent Reference 1 which was applied by the present applicant and laid open to public after priority date of the instant application, it is reported that a selective $5\text{-HT}_{2B}$ and $5\text{-HT}_7$ receptor dual antagonist is useful in treating IBS. Based on the above, it is expected that a compound having the antagonistic activity for $5\text{-HT}_{2B}$ and $5\text{-HT}_7$ receptors is useful as an IBS treating agent.

In addition, since there are reports stating that a selective $5\text{-HT}_{2B}$ and $5\text{-HT}_7$ receptor dual antagonist is useful in preventing migraine (Patent References 2 and 3), it is expected that a compound having the antagonistic activity for $5\text{-HT}_{2B}$ and $5\text{-HT}_7$ receptors is useful also as an agent for preventing migraine.

As the compound having the antagonistic activity for $5\text{-HT}_{2B}$ and $5\text{-HT}_7$ receptors, there are reports of the following Patent References 1 to 3.

In the Patent References 1 to 3, it is reported that a fluoren derivative represented by the following formula (A) has the antagonistic activity for $5\text{-HT}_{2B}$ and $5\text{-HT}_7$ receptors and is useful in preventing migraine (Patent References 2 and 3) and in treating IBS (Patent Reference 1).

(A)

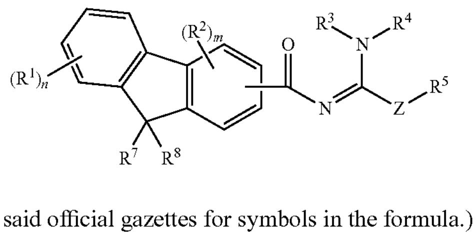

(See said official gazettes for symbols in the formula.)

In addition, as the pyrrole derivatives, there are the following reports.

In the Patent Reference 4, it is reported that a pyrrole derivative represented by the following formula (B) has the androgen receptor antagonism and is effective in treating and preventing hormone-sensitive diseases such as prostatic cancer and the like. However, there are no descriptions on its $5\text{-HT}_{2B}$ and $5\text{-HT}_7$ receptor antagonistic activities and its efficacy for IBS.

(B)

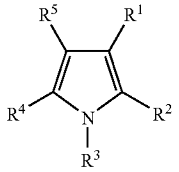

(See said official gazette for symbols in the formula.)

In the Patent Reference 5, it is reported that a pyrrole derivative represented by the following formula (C) has the cannabinoid type 1 receptor antagonism/inverse agonist action and is effective in treating and preventing eating disorder, obesity, type II diabetes, and the like. However, there is no illustrative disclosure as examples of the compound of the present invention, and there are no descriptions on its $5\text{-HT}_{2B}$ and $5\text{-HT}_7$ receptor antagonistic activities and its efficacy for IBS.

(C)

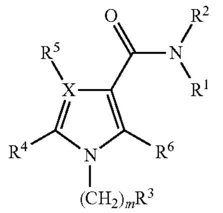

(See said official gazette for symbols in the formula.)

In the Patent Reference 6, it is reported that a pyrrole derivative represented by the following formula (D) has the cannabinoid type 1 receptor antagonism/inverse agonist action and is effective in treating and preventing eating disorder, obesity, type II diabetes, and the like. However, there are no descriptions on its 5-$HT_{2B}$ and 5-$HT_7$ receptor antagonistic activities and its efficacy for IBS.

(D)

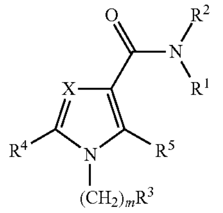

(See said official gazette for symbols in the formula.)

In the Patent Reference 7, it is reported that an N,N'-substituted-1,3-diamino-2-hydroxypropane derivative represented by the following formula (E) has the beta selectase inhibitory action and is effective in treating and preventing Alzheimer disease.

However, there are no descriptions on its 5-$HT_{2B}$ and 5-$HT_7$ receptor antagonistic activities and its efficacy for IBS.

(E)

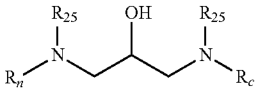

(See said official gazette for symbols in the formula.)

In Non-patent Reference 11, a method for synthesizing 1-benzyl-5-tert-butyl-N-(2-morpholin-4-ylethyl)-2-phenyl-1H-pyrrole-3-carboxamide is reported. However, there are no descriptions on its 5-$HT_{2B}$ and 5-$HT_7$ receptor antagonistic activities and its efficacy for IBS.

In Non-patent Reference 12, it is reported that 1-{[1-benzyl-2-methyl-5-(4-nitrophenyl)-1H-pyrrol-3-yl]carbonyl}-4-methyl piperazine has an antimicrobial activity and is effective for *Candida*. However, there are no descriptions on its 5-$HT_{2B}$ and 5-$HT_7$ receptor antagonistic activities and its efficacy for IBS.

In Non-patent Reference 13 which was published after priority date of the present application, a method for synthesizing 5-tert-butyl-N,1-bis(2-morpholin-4-ylethyl)-2-propyl-1H-pyrrole-3-carboxamide, N,1-bis(2-morpholin-4-ylethyl)-5-phenyl-2-propyl-1H-pyrrole-3-carboxamide, 4-(1-{[5-phenyl-1-(2-phenylethyl)-2-propyl-1H-pyrrol-3-yl]carbonyl}piperidin-4-yl)morpholine and 1-{[2-(4-chlorophenyl)-5-ethyl-1-(pyridine-2-ylmethyl)-1H-pyrrol-3-yl]carbonyl}-N,N-diethylpyrrolidine-3-amine is reported. However, there are no descriptions on their 5-$HT_{2B}$ and 5-$HT_7$ receptor antagonistic activities and their efficacy for IBS.

In addition, 1-[(2-chlorophenyl)sulfonyl]-4-{[2,5-dimethyl-1-(2-thienylmethyl)-1H-pyrrol-3-yl]carbonyl}piperazine (CAS Registry No. 878918-78-6) is known as a catalogue compound. However, there is no report on its 5-$HT_{2B}$ and 5-$HT_7$ receptor antagonistic activities and its efficacy for IBS.

Non-patent Reference 1: "Pharmacological Reviews", (USA), 1994, vol. 46, p. 157-203
Non-patent Reference 2: "Gut", (England), 1998, vol. 42. p. 42-46
Non-patent Reference 3: "The American Journal of Gastroenterology", (USA), 2000, vol. 95, p. 2698-2709

Non-patent Reference 4: "The American Journal of Gastroenterology", (USA), 2003, vol. 98, p. 750-758
Non-patent Reference 5: "Drugs", (New Zealand), 2001, vol. 61, no. 3, p. 317-332
Non-patent Reference 6: "British Journal of Pharmacology", (England), 1995, vol. 114, p. 1525-1527
Non-patent Reference 7: "British Journal of Pharmacology", (England), 2002, vol. 135, p. 1144-1151
Non-patent Reference 8: "European Journal of Pharmacology", (Holland), 1995, vol. 280, p. 243-250
Non-patent Reference 9: "Life Science", (Holland), 2001, vol. 69, p. 2467-2475
Non-patent Reference 10: "British Journal of Pharmacology", (England), 2003, vol. 138, p. 1210-1214
Non-patent Reference 11: "European Journal of Organic Chemistry", (Germany), 2005, vol. 24, p. 5277-5288
Non-patent Reference 12: "Il Farmaco", (Italy), 1992, vol. 47, p. 1047-1053
Non-patent Reference 13: "Journal of Combinatorial Chemistry", (USA), 2006, vol. 8, p. 491-499
Patent Reference 1: International Publication No. 2006/085510 pamphlet
Patent Reference 2: International Publication No. 2005/79845 pamphlet
Patent Reference 3: International Publication No. 2005/80322 pamphlet
Patent Reference 4: US Patent Application Publication No. 2005/0101657 specification
Patent Reference 5: International Publication No. 2004/60870 pamphlet
Patent Reference 6: International Publication No. 2005/108393 pamphlet
Patent Reference 7: International Publication No. 2003/040096 pamphlet

DISCLOSURE OF THE INVENTION

Problems that the Invention is to Solve

As described in the above, the existing therapeutic agents for IBS are not satisfactory from the viewpoints of the efficacy, safety and the like, so that great concern has been directed toward the provision of a novel therapeutic agent for IBS.

Means for Solving the Problems

As described in the above, it is expected that a compound having the antagonistic activity for 5-$HT_{2B}$ and 5-$HT_7$ receptors becomes an excellent therapeutic agent for IBS. Accordingly, the present inventors have conducted intensive studies on a compound having the antagonistic activity for 5-$HT_{2B}$ and 5-$HT_7$ receptors in order to provide a compound useful as a therapeutic agent for IBS. As a result, it was found that novel pyrrole derivatives represented by the following general formula (I) has excellent antagonism for both of the 5-$HT_{2B}$ and 5-$HT_7$ receptors. In addition, by finding that these pyrrole derivatives have superior IBS treating effect in comparison with the conventional compounds which have the antagonistic activity for only one of the 5-$HT_{2B}$ and 5-$HT_7$ receptors, the present invention has been accomplished.

That is, the present invention relates to a pyrrole derivative represented by a general formula (I) or a pharmaceutically acceptable salt thereof.

(I)

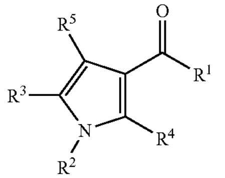

[Symbols in the formula have the following meanings:

$R^1$: —N═C($NH_2$)$_2$, —$NR^{11}R^{12}$ or $R^{13}$, $R^{11}$: —H, lower alkyl or lower alkylene-aryl, wherein the aryl in $R^{11}$ may be substituted, $R^{12}$: nitrogen-containing saturated heterocyclic group (which has a linkage on a carbon atom as the ring atom), lower alkylene-N($R^{14}$)$_2$, lower alkylene-nitrogen-containing saturated heterocyclic group, lower alkylene-C(O)—$R^{13}$ or lower alkylene-$R^{15}$, with the proviso that the lower alkylene and nitrogen-containing saturated heterocyclic group in $R^{12}$ may be respectively substituted, $R^{13}$: nitrogen-containing saturated hetero ring which has a linkage on a nitrogen atom as the ring atom and may be substituted, with the proviso that when the nitrogen atom contained in the nitrogen-containing saturated hetero ring in $R^{13}$ is one, the nitrogen-containing saturated hetero ring is substituted with at least one group selected from a group G, $R^{14}$: the same or different from each other, and each represents —H, lower alkyl, lower alkylene-$OR^0$, lower alkylene-aryl or aryl, wherein the aryl in $R^{14}$ may be substituted, $R^0$: each independently —H or lower alkyl, $R^{15}$: cycloalkyl, aryl or heterocyclic group, which is respectively substituted with a group selected from the group G and may be further substituted, group G: —N($R^{14}$)$_2$, nitrogen-containing saturated heterocyclic group, -lower alkylene-N($R^{14}$)$_2$ and -lower alkylene-nitrogen-containing saturated heterocyclic group, wherein the nitrogen-containing saturated heterocyclic group in the group G may be substituted, $R^3$: lower alkyl, halogeno-lower alkyl, cycloalkyl, hetero ring, aryl, lower alkylene-cycloalkyl, lower alkylene-aryl, lower alkylene-$OR^0$, lower)alkylene-N($R^0$)$_2$ or —C(O)—$R^0$, wherein the aryl and heterocyclic group in $R^3$ may be substituted, $R^4$: lower alkyl, cycloalkyl, aryl or heterocyclic group, wherein the aryl and heterocyclic group in $R^4$ may be substituted, $R^5$: —H, lower alkyl, lower alkylene-$OR^0$, —C(O)—$R^0$, cycloalkyl, aryl or hetero ring, wherein the aryl and heterocyclic group in $R^5$ may be substituted, wherein (I) when $R^1$ is —N═C($NH_2$)$_2$, then

[$R^2$: —H, aryl, heterocyclic group, lower alkyl, cycloalkyl, lower alkylene-$R^{21}$ or —O-lower alkylene-aryl, wherein the lower alkylene, cycloalkyl, aryl and heterocyclic group in $R^2$ may be substituted, and $R^{21}$: aryl, —O-aryl, —O-lower alkylene-aryl, cycloalkyl, heterocyclic group, —CN, —S-lower alkyl, —S(O)-lower alkyl, —S(O)$_2$-lower alkyl, —C(O)-aryl or —$OR^0$, wherein the aryl and heterocyclic group in $R^{21}$ may be substituted], and (II) when $R^1$ is —$NR^{11}R^{12}$ or $R^{13}$, then

[$R^2$: lower alkylene-aryl, lower alkylene-heterocyclic group or —O-lower alkylene-aryl, wherein the lower alkylene, aryl and heterocyclic group in $R^2$ may be substituted], with the proviso that 1 benzyl-2,5-dimethyl-4-(4-nitrophenyl)-N-(2-piperidin-1-ylethyl)-1H-pyrrole-3-carboxamide, N-{1-(3,5-difluorobenzyl)-3-[(3-ethylbenzyl)amino-2-hydroxypropyl}-2,5-dimethyl-1-(pyridin-4-ylmethyl)-1H-pyrrole-3-carboxamide, 5-[2,5-bis(trifluoromethyl)phenyl]-N-(2-hydroxy-3-morpholin-4-ylpropyl)-2-methyl-1-{[tetrahydrofuran-2-yl]methyl}-1H-pyrrole-3-carboxamide, 1-benzyl-5-tert-butyl-N-(2-morpholin-4-ylethyl)-2-phenyl-1H-pyrrole-3-carboxamide, 1-{[1-benzyl-2-methyl-5-(4-nitrophenyl)-1H-pyrrol-3-yl]carbonyl}-4-methylpiperazine, and 1-[(2-chlorophenyl)sulfonyl]-4-{[2,5-dimethyl-1-(2-thienylmethyl)-1H-pyrrol-3-yl]carbonyl}piperazine are excluded. The same shall apply hereinafter.]

In addition, the present invention also relates to a pharmaceutical composition which comprises the aforementioned pyrrole derivative or a pharmaceutically acceptable salt thereof and a pharmaceutically acceptable carrier, particularly a pharmaceutical composition which is a 5-$HT_{2B}$ receptor and 5-$HT_7$ receptor dual antagonist or an agent for treating irritable bowel syndrome.

That is, (1) a pharmaceutical composition which comprises the compound described in formula (I) or a pharmaceutically acceptable salt thereof and a pharmaceutically acceptable carrier.

(2) The pharmaceutical composition described in (1), which is a 5-$HT_{2B}$ receptor and 5-$HT_7$ receptor dual antagonist.

(3) The pharmaceutical composition described in (1), which is an agent for treating irritable bowel syndrome.

(5) Use of the compound described in formula (I) or a pharmaceutically acceptable salt thereof for the manufacture of a 5-$HT_{2B}$ receptor and 5-$HT_7$ receptor dual antagonist or an agent for treating irritable bowel syndrome.

(6) A method for treating irritable bowel syndrome, which comprises administering a therapeutically effective amount of the compound described in formula (I) or a salt thereof to a patient.

Effect of the Invention

As is described later, the compound of the present invention showed excellent antagonistic activity for both of the 5-$HT_{2B}$ and 5-$HT_7$ receptors. In addition, the compound of the present invention showed superior IBS treating effect in comparison with the conventional compounds which have the antagonistic activity for only one of the 5-$HT_{2B}$ and 5-$HT_7$ receptors. Based on this, the compound of the present invention is useful as an IBS treating agent.

BEST MODE FOR CARRYING OUT THE INVENTION

Figure 1:
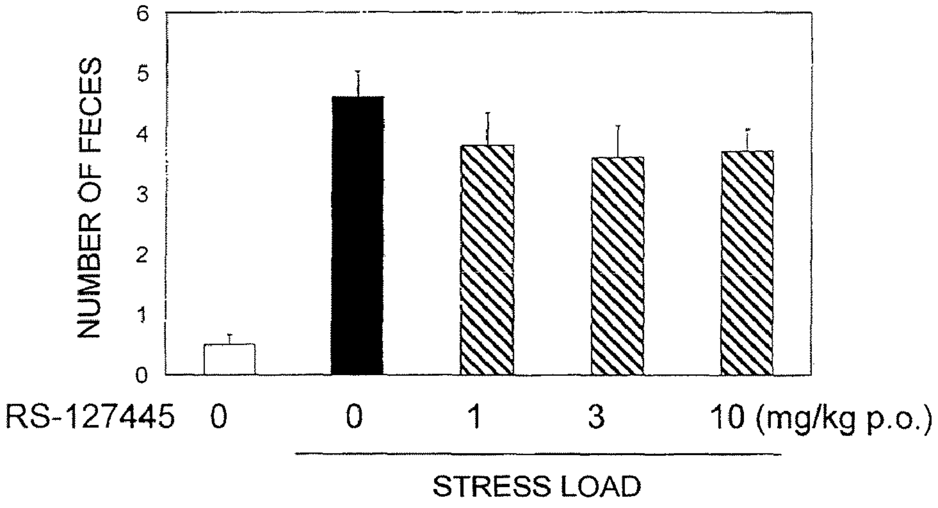
FIG. 1 is a graph showing a result of the measurement of the number of faces excreted at the time of RS-127445 administration, in the rat restraint stress defecation model of the test method (4). Significant difference was not found in the 1, 3 or 10 mg/kg administration group in comparison with the non-administration group (N=10).

Further detailed description of the present invention is as follows.

Each of the terms "lower alkyl" and "lower alkylene" as used herein means a straight or branched hydrocarbon chain having from 1 to 6 carbon atoms (to be referred sometimes to as $C_{1-6}$ hereinafter) unless otherwise noted.

Thus, the "lower alkyl" means a $C_{1-6}$ alkyl, which is illustratively, for example, methyl, ethyl, propyl, butyl, pentyl or hexyl, or structural isomer thereof such as isopropyl, isobutyl, tert-butyl or the like, preferably a $C_{1-4}$ alkyl, more preferably methyl, ethyl, propyl, isopropyl and tert-butyl.

The "alkylene" means a divalent group in which one hydrogen at an optional position of alkyl is removed. The "lower alkylene" means a $C_{1-6}$ alkylene. Illustratively, it is methylene, ethylene, methylmethylene, dimethylmethylene, propylene, butylene, pentylene, hexylene and the like. Preferred is a $C_{1-3}$ alkylene, and more preferred are methylene, ethylene, methylmethylene, dimethylmethylene and propylene.

The "cycloalkyl" means a $C_{3-10}$ non-aromatic hydrocarbon ring which may form a bridged ring or Spiro ring. In addition, it may partially have an unsaturated bond, and benzene ring may be condensed therewith. However, when benzene ring is condensed, the linkage is present on the non-aromatic ring. Illustratively, for example, cyclopropyl, cyclobutyl, cyclopentyl, cyclohexyl, cyclooctyl, cyclohexenyl, cyclooctanedienyl, adamantyl, norbornyl, indanyl having linkages at the 1- to 3-positions and the like may be cited, and preferred is cyclopropyl, cyclobutyl, cyclopentyl or cyclohexyl.

The "halogen" means a halogen atom, and for example, fluoro, chloro, bromo, iodo and the like may be illustratively cited, of which fluoro or chloro is preferable.

The "halogeno-lower alkyl" means a group in which one or more of optional hydrogen atoms of the aforementioned "lower alkyl" are substituted with the aforementioned "halogen" that are the same or different from each other. Illustratively, fluoromethyl, difluoromethyl, trifluoromethyl, trifluoroethyl, pentafluoroethyl and the like may be exemplified. Preferred are fluoromethyl, difluoromethyl and trifluoromethyl, more preferred is trifluoromethyl.

The "aryl" means a monocyclic to tricyclic $C_{6-14}$ aromatic hydrocarbon ring, and for example, phenyl, naphthyl and the like may be illustratively cited, of which phenyl is preferable. In addition, a $C_{5-8}$ cycloalkyl ring may be condensed therewith. However, when the cycloalkyl ring is condensed, the linkage is present on the aromatic ring. For example, indanyl having linkages at the 4- to 7-positions or tetrahydronaphthyl having linkages at the 5- to 8-positions may be formed.

The "hetero ring" means a monocyclic 3- to 12-membered saturated, partially unsaturated or aromatic monocyclic hetero ring, a bicyclic hetero ring in which said monocyclic hetero rings are mutually condensed or said monocyclic hetero ring is condensed with cycloalkyl ring or benzene ring, or tricyclic hetero ring in which said bicyclic hetero ring is condensed with a monocyclic hetero ring, cycloalkyl ring or benzene ring, which contains 1 to 4 hetero atoms selected from O, S and N. The S or N as a ring atom may be oxidized to form an oxide or dioxide, or may form a bridged ring or spiro ring. As the monocyclic hetero ring, for example, pyrrolyl, furyl, thienyl, oxazolyl, isoxazolyl, oxadiazolyl, thiazolyl, thiadiazolyl, imidazolyl, triazolyl, tetrazolyl, pyridyl, pyridazinyl, pyrimidinyl, pyrazinyl, azolizinyl, azetidinyl, oxetanyl, pyrrolidinyl, piperidinyl, piperazinyl, morpholinyl, homopiperidinyl, homomorpholinyl, tetrahydrofuranyl, tetrahydropyranyl, tetrahydrothiopyranyl and the like may be cited. As the bicyclic hetero ring, for example, indolyl, benzofuranyl, benzothienyl, benzoxazolyl, benzoisoxazolyl, benzoimidazolyl, benzothiazolyl, benzothiadiazolyl, quinolyl, isoquinolyl, quinazolinyl, quinoxalinyl, cinnolinyl, indolinyl, tetrahydroquinolinyl, tetrahydroisoquinolinyl, octahydropyrolo[1,2-a]pyrazinyl, octahydro-2H-pyrido[1,2-a]pyrazinyl and the like may be cited. As the tricyclic hetero ring, for example, carbazolyl, phenoxazinyl, fluorenyl and the like may be cited. As the bridged ring, quinuclidinyl, 3,8-diazabicyclo[3.2.1]octanyl and the like may be cited. The hetero ring is preferably furyl, thienyl, pyridyl, azetidinyl, pyrrolidinyl, piperidinyl, piperazinyl, morpholinyl, tetrahydrofuranyl, tetrahydropyranyl or quinuclidinyl.

The "nitrogen-containing saturated hetero ring" means a saturated hetero ring among the aforementioned "hetero ring", which contains one or more nitrogen atoms. For example, azetidinyl, pyrrolidinyl, piperidinyl, piperazinyl, morpholinyl, homopiperidinyl, homomorpholinyl, quinuclidinyl, 3,8-diazabicyclo[3.2.1]octanyl, octahydropyrolo-[1,2-a]pyrazinyl, octahydro-2H-pyrido[1,2-a]pyrazinyl and the like may be cited. Preferred are azetidinyl, pyrrolidinyl, piperidinyl, piperazinyl, morpholinyl and quinuclidinyl.

The "may be substituted" means "not substituted" or "substituted with 1 to 5 substituent groups which may be the same or different from one another".

The acceptable substituent group of the term "may be substituted" as used herein may be any substituent group which is generally used in said technical field as the substituent group of respective groups. In addition, when there are two or more groups like the case of the $R^0$ of —C(O)N($R^0$)$_2$, the respective groups may be the same or different from each other.

A group selected from the following group $G^1$ may be exemplified as a preferred acceptable substituent group of the "aryl" which may be substituted in $R^{11}$, "aryl" which may be substituted in $R^{14}$, "nitrogen-containing saturated heterocyclic group" which may be substituted in the group G, "aryl" and "heterocyclic group" which may be substituted in $R^4$, and "aryl" and "heterocyclic group" which may be substituted in $R^5$.

Group $G^1$: halogen, lower alkyl, —$OR^0$, —O-halogeno-lower alkyl and oxo.

As the acceptable substituent group of the "lower alkylene" which may be substituted in $R^{12}$, a group selected from halogen and aryl may be preferably cited.

As the acceptable substituent group of the "nitrogen-containing saturated heterocyclic group" which may be substituted in $R^{12}$, a group selected from the following group $G^2$ may be preferably cited. More preferred is halogen, lower alkyl, halogeno-lower alkyl, —$OR^0$ or —O-halogeno-lower alkyl, and further preferred is lower alkyl.

Group $G^2$: halogen, lower alkyl, halogeno-lower alkyl, —$OR^0$, —O-halogeno-lower alkyl, lower alkylene-$OR^0$, lower alkylene-N($R^0$)$_2$, lower alkylene-cycloalkyl, lower alkylene-aryl, —CH(aryl)$_2$, lower alkylene-O-aryl, lower alkylene-hetero ring, cycloalkyl, aryl and hetero ring.

With the proviso that the aryl and heterocyclic group in the group $G^2$ may be substituted with a group selected from the aforementioned group $G^1$.

As the acceptable substituent group in the "nitrogen-containing saturated heterocyclic group" which may be substituted in $R^{13}$, and the "cycloalkyl", "aryl" and "heterocyclic group" which are respectively substituted with a group selected from the group G and may further be substituted in $R^{15}$, groups selected from the group G and the aforementioned group $G^2$ may be preferably exemplified. More preferred is a group selected from the group G, or halogen, lower alkyl, halogeno-lower alkyl, —$OR^0$ or —O-halogeno-lower alkyl, and further preferred is a group selected from the group G or halogen.

As the acceptable substituent group in the "aryl" and "heterocyclic group" which may be substituted in $R^2$, the "aryl" and "heterocyclic group" which may be substituted in $R^{21}$, and the "aryl" and "heterocyclic group" which may be respectively substituted in $R^3$, groups selected from the following group $G^3$ may be preferably exemplified. More preferred is halogen, lower alkyl, halogeno-lower alkyl, —$OR^0$ or —O-halogeno-lower alkyl, and further preferred is halogen.

Group $G^3$: halogen, nitro, cyano, lower alkyl, halogeno-lower alkyl, —$OR^0$, —O-halogeno-lower alkyl, —N($R^0$)$_2$, —S-lower alkyl, —S(O)-lower alkyl, —S(O)$_2$-lower alkyl, oxo, cycloalkyl, aryl and hetero ring.

In this regard, the aryl and heterocyclic group in the group G may be substituted with a group selected from the aforementioned group G.

As the acceptable substituent group in the "cycloalkyl" which may be substituted in $R^2$, groups selected from the following group $G^4$ may be preferably exemplified.

Group $G^4$: halogen, lower alkyl, halogeno-lower alkyl, —$OR^0$, —O-halogeno-lower alkyl, —N($R^0$)$_2$, —S-lower alkyl, —S(O)-lower alkyl and —S(O)$_2$-lower alkyl.

As the acceptable substituent group in the "lower alkylene" which may be substituted in $R^2$, a group selected from halogen and —$OR^0$ may be preferably exemplified.

Preferred embodiments of the present invention are shown in the following.

(1) Preferred as $R^1$ is —N═C(NH$_2$)$_2$, —N($R^0$)-(nitrogen-containing saturated heterocyclic group which has a linkage on a ring atom carbon atom and may be substituted), —N($R^0$)-lower alkylene-N(lower alkyl)$_2$, —N($R^0$)-lower alkylene-(nitrogen-containing saturated heterocyclic group which may be substituted), —N($R^0$)-lower alkylene-(heterocyclic group substituted with —N(lower alkyl)$_2$) or —N($R^0$)-lower alkylene-(cycloalkyl substituted with —N(lower alkyl)$_2$), more preferred is —N═C(NH$_2$)$_2$, —N($R^0$)-(nitrogen-containing saturated heterocyclic group which has a linkage on a ring atom carbon atom and may be substituted), —N($R^0$)-lower alkylene-N(lower alkyl)$_2$ or —N($R^0$)-lower alkylene-(nitrogen-containing saturated heterocyclic group which may be substituted), further preferred is —N═C(NH$_2$)$_2$, —N($R^0$)-(nitrogen-containing saturated heterocyclic group which has a linkage on a ring atom carbon atom and may be substituted), —N($R^0$)-lower alkylene-N(lower alkyl)$_2$ or —N($R^0$)-lower alkylene-(nitrogen-containing saturated heterocyclic group which may be substituted with lower alkyl), further preferred is —N═C(NH$_2$)$_2$, —NH-(nitrogen-containing saturated heterocyclic group which has a linkage on a ring atom carbon atom and may be substituted with lower alkyl) or —NH-lower alkylene-(nitrogen-containing saturated heterocyclic group which may be substituted with lower alkyl), and particularly preferred is —NH-(nitrogen-containing saturated heterocyclic group which has a linkage on a ring atom carbon atom and may be substituted with lower alkyl).

(2) Preferred as $R^2$ is aryl, lower alkylene-(aryl which may be substituted) or lower alkylene-(heterocyclic group which may be substituted), more preferred is lower alkylene-(phenyl which may be substituted), further preferred is lower alkylene-(phenyl which may be substituted with halogen), further more preferred is —(CH$_2$)$_2$-(phenyl which may be substituted with halogen) and particularly preferred is —(CH$_2$)$_2$-(phenyl which is substituted with halogen).

(3) Preferred as $R^3$ is lower alkyl, cycloalkyl, aryl which may be substituted or heterocyclic group which may be substituted, more preferred is lower alkyl, and further preferred is tert-butyl.

(4) Preferred as $R^4$ is lower alkyl, and more preferred is methyl.

(5) Preferred as $R^5$ is —H or lower alkyl, and more preferred is —H.

As other preferred embodiment, a compound consisting of the respective groups described in the above-mentioned (1) to (5) is desirable.

In addition, further other preferred embodiments of the present invention are shown in the following.

(1) The compound described in the formula (I), wherein $R^5$ is —H or lower alkyl.

(2) The compound described in (1), wherein $R^4$ is lower alkyl.

(3) The compound described in (2), wherein $R^3$ is lower alkyl.

(4) The compound described in (3), wherein $R^2$ is lower alkylene-(phenyl which may be substituted with halogen).

(5) The compound described in (4), wherein $R^1$ is —N═C(NH$_2$)$_2$, —N($R^0$)-(nitrogen-containing saturated heterocyclic group which has a linkage on a carbon atom as the ring atom and may be substituted with lower alkyl), —N($R^0$)-lower alkylene-N(lower alkyl)$_2$ or —N($R^0$)-lower alkylene-(nitrogen-containing saturated heterocyclic group which may be substituted with lower alkyl).

(6) A compound described in the formula (I), which is selected from the group consisting of 5-tert-butyl-1-[2-(4-fluorophenyl)ethyl]-2-methyl-N-[(3S)-1-methylpyrrolidin-3-yl]-1H-pyrrole-3-carboxamide, 5-tert-butyl-1-[2-(4-fluorophenyl)ethyl]-2-methyl-N-[(3R)-1-methylpyrrolidin-3-yl]-1H-pyrrole-3-carboxamide, 5-tert-butyl-1-[2-(4-fluorophenyl)ethyl]-2,4-dimethyl-N-[(3S)-1-methylpyrrolidin-3-yl]-1H-pyrrole-3-carboxamide and 5-tert-butyl-1-[2-(4-fluorophenyl)ethyl]-2,4-dimethyl-N-[(3S)-1-methylpyrrolidin-3-yl]-1H-pyrrole-3-carboxamide, or a pharmaceutically acceptable salt thereof.

In addition, the "binding affinity" as used herein means the ability of a compound to be tested to bind to a part of a receptor, and evaluation of this is carried out by, as described in the test method, comparing the Ki value calculated by the in vitro receptor binding test or the $IC_{50}$ value of a receptor binding test carried out under the same conditions as occasion demands. In this connection, when a sufficient inhibitory action is not shown at a predetermined concentration in the receptor binding test so that the $IC_{50}$ value cannot be calculated, the $IC_{50}$ value of the compound is regarded in some cases as said concentration or more.

When binding affinity of the compound of the present invention for the 5-$HT_{2B}$ and 5-$HT_7$ receptors is "selective" in comparison with other receptors, it means that the binding affinity for said receptors is high in comparison with the binding affinity for "other receptors". According to the present invention, the "selective" means a case in which the Ki value or $IC_{50}$ value showing the binding affinity for said receptors is 1/10 or less in comparison with the value for "other receptors", and this value is more preferably 1/50 or less, further preferably 1/100 or less, more further preferably 1/500 or less, and particularly preferably 1/1000 or less.

In this connection, the "other receptors" are receptors other than 5-$HT_{2B}$ and 5-$HT_7$ receptors, which have been reported in relation to the existing nonselective 5-HT receptor antagonists, and are receptors which are particularly concerned in undesirable actions. Thus, preferred as the compounds of the present invention are compounds whose binding affinity for 5-$HT_{2B}$ and 5-$HT_7$ receptors is selective in comparison with $\alpha_1$, $M_1$ and $D_2$ receptors, and more preferred are compounds whose binding affinity for 5-$HT_{2B}$ and 5-$HT_7$ receptors is selective in comparison with $\alpha_1$, $M_1$, $D_2$, 5-$HT_{1A}$, 5-$HT_{1B}$, 5-$HT_{2A}$, 5-$HT_{2C}$, 5-$HT_3$, 5-$HT_4$ and 5-$HT_6$ receptors.

There are cases in which geometrical isomers and tautomers are present in the compound (I) of the present invention. For example, the following tautomers are present. Even when described as one side of the configurations in this description, the present invention is not limited to the one side of the configurations.

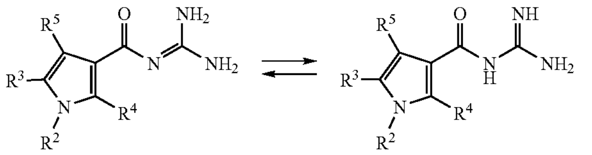

The present invention includes one of such tautomers or a mixture thereof.

In addition, the compound of the present invention exists in isomer forms based on asymmetric carbon atom in some cases. The present invention includes mixtures of these optical isomers and isolated forms thereof.

In this connection, all of the compounds which are converted into the compounds (I) or salts thereof in the living body by undergoing metabolism, so-called prodrugs, are also included in the compound (I) of the present invention. As the groups which form such prodrugs, the groups described in "Progress in Medicine", Lifescience Medica, 1985, vol. 5, p. 2157-2161, and the groups described in "Iyakuhin no Kaihatsu (Development of Medicines)", vol. 7, Bunshi Sekkei (Molecular Design), 163-198, published in 1990 by Hirokawa Shoten, may be exemplified.

As the pharmaceutically acceptable salt of the compound (I) of the present invention, illustratively, acid addition salts with inorganic acids (e.g., hydrochloric acid, hydrobromic acid, hydriodic acid, sulfuric acid, nitric acid, phosphoric acid and the like), organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), and the like may be exemplified. Also, there is a case in which it forms a salt with a base depending on the kind of substituent group, and for example, salts with inorganic bases including metals (e.g., sodium, potassium, magnesium, calcium, aluminum and the like) or with organic bases (e.g., methylamine, ethylamine, ethanolamine, lysine, ornithine and the like), ammonium salts, and the like may be exemplified.

In addition, the present invention also includes various hydrates and solvates and polymorphism of the compound (I) of the present invention or a pharmaceutically acceptable salt thereof.

(Production Methods)

The compound (I) of the present invention and a pharmaceutically acceptable salt thereof may be produced by employing various known synthesis methods making use of the characteristics based on its basic skeleton or kind of the substituent groups. In that case, depending on the kind of functional group, there is an effective case from the production technology point of view to protect said functional group with an appropriate protecting group at the stage of starting materials to intermediates, or to replace it with a group which may be easily converted into said functional group. Examples of such a functional group include amino group, hydroxyl group, carboxyl group and the like, and as their protecting groups, the protecting groups described for example in "Protective Groups in Organic Synthesis" edited by T. W. Greene and P. G. Wuts, (USA), 3rd edition, John Wiley & Sons, 1999, may be cited, which may be optionally selected and used in response to the reaction conditions. By such a method, a desired compound may be obtained by introducing said protecting group and carrying out the reaction, and then removing the protecting group as occasion demands or converting it into a desired group.

The following describes typical production methods of the compounds of the present invention.

(First Production Method)

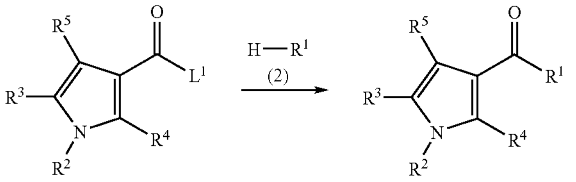

(1) (I)

(In the formulae, $L^1$ represents —OH or a leaving group such as —O-lower alkyl, halogen, —O-methanesulfonyl, —O-toluenesulfonyl or the like. The same shall apply hereinafter.)

The compound (I) of the present invention may be produced by subjecting the compound represented by (1) which is a carboxylic acid or a reactive derivative thereof and an amine derivative (2) to amidation reaction.

When the starting compound (I) is used as a free carboxylic acid wherein $L^1$ is —OH, a method in which the compound (1) and amine derivative (2) are dehydration-condensed in the presence of a condensing agent is used. As the condensing agent in this case, it is desirable to use N,N'-dicyclohexylcarbodiimide (DCC), 1-[3-(dimethylamino)propyl]-3-ethylcarbodiimide (WSC), 1,1'-carbonyldiimidazole (CDI), 2-(1H-benzotriazol-1-yl)-1,1,3,3-tetramethyluronium hexafluorophosphate (HBTU), diphenylphosphoryl azide (DPPA), phosphorus oxychloride, PS-Carbodiimide (Argonaut Technologies, Inc., USA) or the like, and further an additive agent as occasion demands (e.g., N-hydroxysuccinimide (HONSu), 1-hydroxybenzotriazole (HOBt) or the like).

The reaction is carried out using the compound (1) and amine derivative (2) in equivalent amount or one of them in excess amount, and using a condensing agent in equivalent amount or excess amount based on the carboxylic acid. It may be carried out under cooling to heating, preferably at from −20° C. to 60° C., in a reaction inert solvent such as aromatic hydrocarbons such as benzene, toluene, xylene or the like, halogenated hydrocarbons such as dichloromethane, 1,2-dichloroethane, chloroform or the like, ethers such as diethyl ether, tetrahydrofuran (THF), dioxane, dimethoxyethane (DME) or the like, N,N-dimethylformamide (DMF), dimethyl sulfoxide (DMSO), ethyl acetate, acetonitrile, water or the like, or a mixed liquid thereof.

When the starting compound (I) is used as a compound wherein $L^1$ is a leaving group, namely a reactive derivative of the carboxylic acid, an acid halide (acid chloride, acid bromide or the like), an acid anhydride (a mixed acid anhydride with phenyl carbonate, p-toluenesulfonic acid, isovaleric acid or the like or symmetric acid anhydride), an active ester (an ester which may be prepared using phenol which may be substituted with an electron withdrawing group such as nitro group, fluorine atom or the like, HOBt, HONSu or the like), a lower alkyl ester or the like may be used as the reactive derivative of carboxylic acid. Each of these reactive derivatives may be produced from the carboxylic acid using a reaction obvious to those skilled in the art.

The reaction may be carried out using the compound (1) and amine derivative (2) in equivalent amount or one of them in excess amount under cooling to heating, preferably at from −20° C. to 60° C., in a reaction inert solvent such as aromatic hydrocarbons, halogenated hydrocarbons, ethers, N,N-dimethylformamide (DMF), dimethyl sulfoxide (DMSO), ethyl acetate, acetonitrile, water or the like, or a mixed liquid thereof. In this connection, when a lower alkyl ester is used as the reactive derivative, it is desirable to carry out the reaction under room temperature to heating. Depending on the kind of the reactive derivative, it is sometimes advantageous for smoothly carrying out the reaction to undergo the reaction in the presence of a base (organic bases such as triethylamine, diisopropylethylamine, N-methylmorpholine, pyridine, 4-(N,N-dimethylamino)pyridine or the like, or inorganic base such as sodium bicarbonate or the like). Pyridine can also serve as the solvent.

(Second Production Method A)

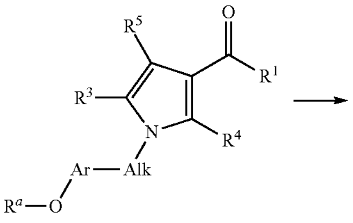

(I-a)

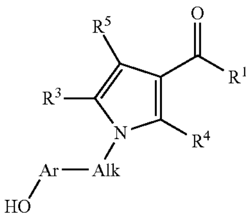

(I-b)

(In the formulae, $R^a$ represents lower alkyl, and Alk represents lower alkylene and Ar represents aryl.)

Among the compound (I) of the present invention, a compound represented by the general formula (I-b) may be produced by subjecting a compound of the present invention represented by the general formula (I-a) to an ether bond-cleaving reaction.

The reaction is carried out by treating the compound (I-a) with an equivalent amount or excess amount of an acid (e.g., a Bronsted acid such as hydrobromic acid, hydriodic acid, trifluoroacetic acid or the like or a Lowis acid such as aluminum trichloride, boron tribromide, boron trichloride or the like), and for example, the method described in "Jikken Kagaku Koza (Experimental Chemistry Course) (Maruzen)" edited by The Chemical Society of Japan ($4^{th}$ edition, vol. 20, 1992, 237) or the like may be employed.

(Second Production Method B)

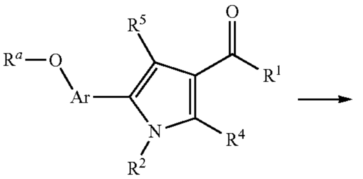

(I-c)

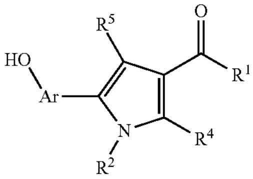

(I-d)

Among the compound (I) of the present invention, a compound represented by the general formula (I-d) may be produced by subjecting a compound of the present invention represented by the general formula (I-c) to an ether bond-cleaving reaction.

The reaction may be carried out in the same manner as in the second production method A.

(Third Method)

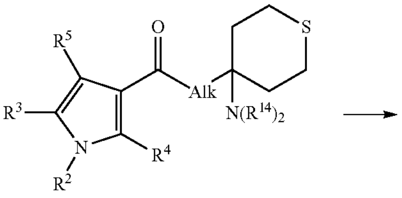

(I-e)

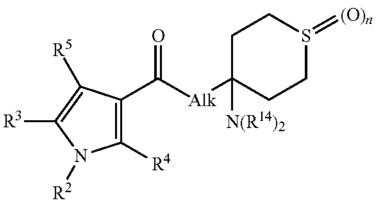

(I-f)

(In the formulae, n represents 1 or 2. The same shall apply hereinafter.)

Among the compound (I) of the present invention, a compound represented by the general formula (I-f) may be produced by subjecting a compound of the present invention represented by the general formula (I-e) to an oxidation reaction.

The reaction is carried out by treating the compound (I-e) with an equivalent or excess amount of an oxidizing agent. As the oxidizing agent, for example, hydrogen peroxide, metachloroperbenzoic acid, sodium metaperiodate, osmium (VII) oxide or ruthenium(VII) oxide is used, and for example, the method described in “Jikken Kagaku Koza (Maruzen)” edited by The Chemical Society of Japan ($4^{th}$ edition, vol. 23, 1991, p. 276), “Jikken Kagaku Koza (Maruzen)” edited by The Chemical Society of Japan ($4^{th}$ edition, vol. 24, 1992, 350) or the like may be employed.

(Fourth Method Other Production Methods)

The compounds of the present invention having various functional groups such as amino group, carboxyl group, amido group, hydroxyl group, alkylamino group, alkoxy and the like may be easily synthesized making use of the methods which are obvious to those skilled in the art or modified methods thereof, using the compounds of the present invention having corresponding nitro group, ester group, carboxyl group, amino group, hydroxyl group and the like as the starting materials. For example, these may be produced by the following reactions.

4-a: Reduction (1)

A compound having amino group may be produced by reducing a compound having nitro group. For example, the reaction may be carried out using a hydrogenation reaction which uses palladium-carbon, Raney nickel or the like as the catalyst.

4-b: Reduction (2)

A compound having a hydroxyalkyl group may be produced by reducing a compound having an ester group. For example, the reaction may be carried out using lithium aluminum hydride, sodium borohydride or the like as the reducing agent.

4-c: Hydrolysis

A compound having carboxyl group may be produced by hydrolyzing a compound having an ester group. For example, it may be carried out in accordance with the deprotection reaction described in the aforementioned “Protective Groups in Organic Synthesis”.

4-d: Amidation

A compound having amido group may be produced by the amidation of a compound having carboxyl group or amino group. For example, it may be carried out in accordance with the aforementioned first production method.

4-e: N-Alkylation

A compound having an alkylamino group may be produced by the alkylation of a compound having amino group. As the alkylation reaction, the reaction may be effected in the usual way using various alkylating agents (e.g., an alkyl halide, an alkyl sulfonate ester and the like). In addition, a compound having an alkylamino group may be produced by the reductive alkylation of a compound having amino group with a carbonyl compound. As the alkylation of amino group, for example, the method described in “Jikken Kagaku Koza (volume 20) Yuki Gosei 2 (Organic Synthesis 2)” edited by The Chemical Society of Japan ($4^{th}$ edition, Maruzen, 1992, p. 300) or the like may be employed.

4-f: O-Alkylation

A compound having an alkoxy group may be produced by alkylating a compound having hydroxyl group. As the alkylation reaction, the reaction may be effected in the usual way using various alkylating agents (e.g., an alkyl halide, an alkyl sulfonate ester and the like). For example, it may be carried out by the method described in “Jikken Kagaku Koza (Maruzen)” edited by The Chemical Society of Japan ($4^{th}$ edition, vol. 20, 1992, p. 187) or the like.

[Production of Starting Compounds]

The starting compounds to be used in the production of the compound (I) of the present invention may be produced for example using the following methods, known methods or modified methods thereof.

(Starting Material Synthesis 1)

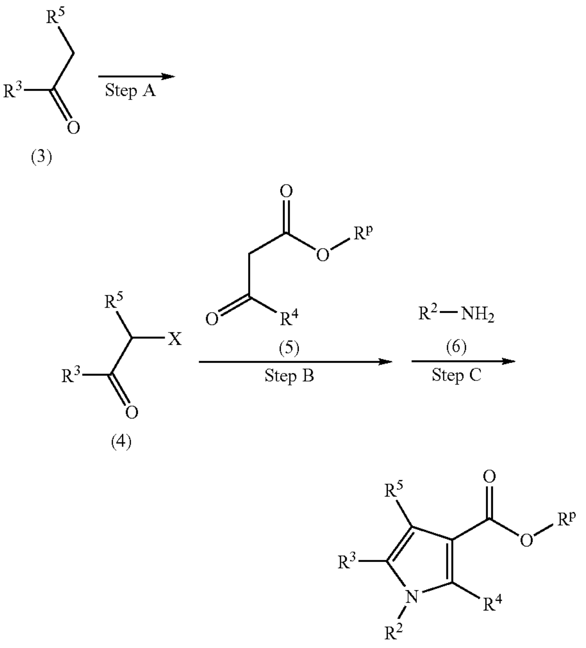

(3)
(4)
(5)
(6)
(7)

(In the formulae, X represents a halogen such as bromo, chloro or the like, and $R^P$ represents a protecting group such as lower alkyl, benzyl or the like. The same shall apply hereinafter.)

In this pathway, the halogenation reaction of step A may be carried out, for example, by the method described in “Jikken Kagaku Koza (Maruzen)” edited by The Chemical Society of Japan ($4^{th}$ edition, vol. 19, 1992, p. 430) or the like. The alkylation reaction of step B may be carried out, for example, by the method described in “Jikken Kagaku Koza (Maruzen)” edited by The Chemical Society of Japan ($4^{th}$ edition, vol. 21, 1991, p. 298) or the like. The pyrrole ring formation reaction of step C may be carried out, for example, by the method described in “Shinpen Hetero Kan Kagobutsu Kiso-hen (New Edition, Heterocyclic Compounds, Fundamental Volume) (Kodansha Scientific)” (2004, p. 134) or the like.

(Starting Material Synthesis 2)

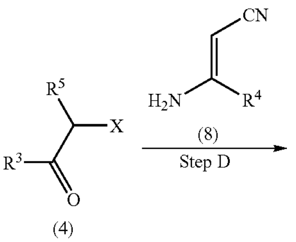

(8)
(4)

-continued

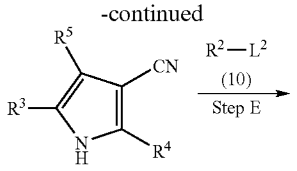

(9)

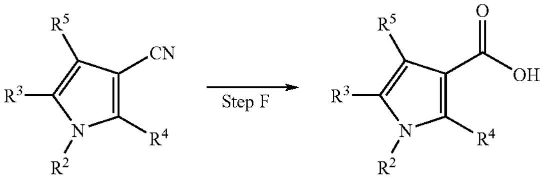

(11) (1-a)

(In the formulae, $L^2$ represents —OH or a leaving group such as halogen, —O-methanesulfonyl, —O-p-toluenesulfonyl or the like. The same shall apply hereinafter.)

In this pathway, the pyrrole ring formation reaction of step D may be carried out, for example, by the method described in "Shinpen Hetero Kan Kagobutsu Kiso-hen (Kodansha Scientific)" (2004, p. 134) or the like. The alkylation reaction of step E may be carried out, for example, by the method described in "Jikken Kagaku Koza (Maruzen)" edited by The Chemical Society of Japan (4th edition, vol. 20, 1992, p. 284) or the like. In addition, when $L^2$ is —OH, it may be carried out under cooling to heating in a reaction inert solvent such as aromatic hydrocarbons, ethers or the like or a mixed liquid thereof using (cyanomethylene)tributylphosphorane or (cyanomethylene)trimethylphospholan. The hydrolysis reaction of step F may be carried out, for example, by the method described in "Jikken Kagaku Koza (Maruzen)" edited by The Chemical Society of Japan (4th edition, vol. 22, 1992, p. 12) or the like.

(Starting Material Synthesis 3A)

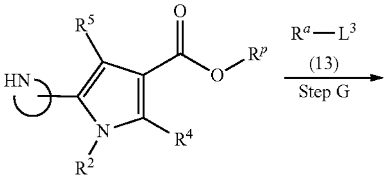

(12)

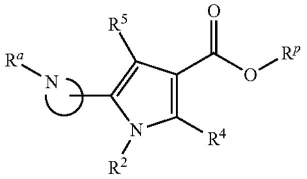

(14)

(In the formulae, $L^3$ represents a leaving group such as halogen, —O-methanesulfonyl, —O-p-toluenesulfonyl or the like, and

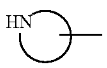

represents a nitrogen-containing hetero ring. The same shall apply hereinafter.)

The N-alkylation reaction of step G may be carried out, for example, by the method described in "Jikken Kagaku Koza (Maruzen)" edited by The Chemical Society of Japan (4th edition, vol. 20, 1992, p. 284).

(Starting Material Synthesis 3B)

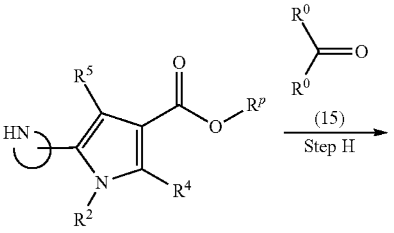

(12)

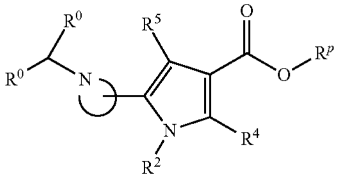

(14-a)

The reductive alkylation reaction of step H may be carried out, for example, by the method described in "Jikken Kagaku Koza (Maruzen)" edited by The Chemical Society of Japan (4th edition, vol. 20, 1992, p. 300) or the like.

(Starting Material Synthesis 4A)

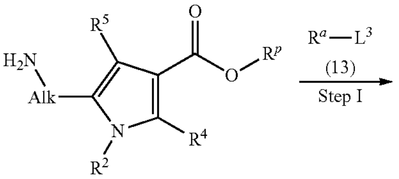

(16)

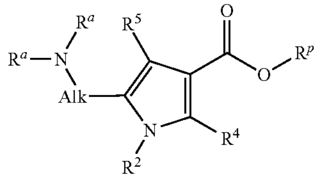

(17)

The N-alkylation reaction of step G may be carried out in the same manner as in the starting material synthesis 3A.

(Starting Material Synthesis 4B)

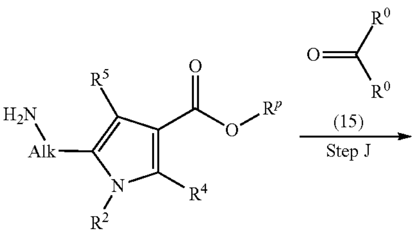

(16)

-continued

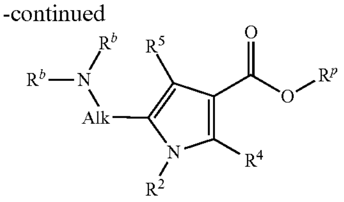

(17)

(In the formula, $R^b$ represents —$CH(R^0)_2$. The same shall apply hereinafter.)

The reductive alkylation reaction of step J may be carried out in the same manner as in the starting material synthesis 3B.

(Starting Material Synthesis 5)

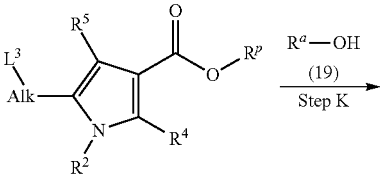

(18)

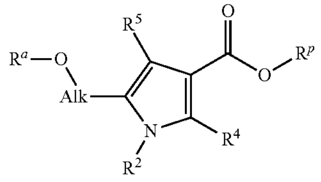

(20)

The O-alkylation reaction of step K may be carried out, for example, by the method described in "Jikken Kagaku Koza (Maruzen)" edited by The Chemical Society of Japan (4$^{th}$ edition, vol. 20, 1992, p. 187) or the like.

(Starting Material Synthesis 6)

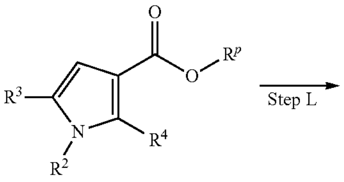

(21)

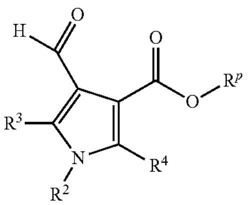

(22)

The formyl reaction of step L may be carried out, for example, by the method described in "Jikken Kagaku Koza (Maruzen)" edited by The Chemical Society of Japan (4$^{th}$ edition, vol. 21, 1991, p. 106) or the like.

(Starting Material Synthesis 7)

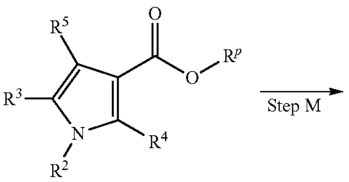

(7)

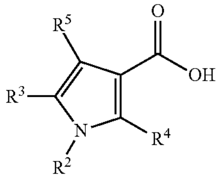

(1-a)

The deprotection reaction of step M may be carried out, for example, in accordance with the aforementioned method described in "Protective Groups in Organic Synthesis".

The compound (I) produced in this manner may be isolated and purified as a free compound, a salt thereof, or various solvates (e.g., hydrates or the like). Salts may be produced by the general salt formation treatment. The isolation and purification are carried out by employing general chemical operations such as extraction, concentration, crystallization, filtration, recrystallization, various types of chromatography and the like.

Various types of isomers may be isolated in the usual way making use of the difference in the physicochemical properties between isomers. For example, optical isomers may be respectively separated and purified by techniques such as the method in which racemic compounds are introduced into diastereomer salts with optically active organic acid (tartaric acid or the like) and then subjected to a fractional crystallization; the method using a chiral filler-aided column chromatography; or the like. In addition, an optically active compound can also be produced using an appropriate optically active compound as the starting material. In this connection, a diastereomer mixture can also be separated by a fractional crystallization, chromatography or the like.

The pharmaceutical preparation which comprises one or two or more species of the compound of the present invention or a salt thereof as the active ingredient is prepared using carriers, fillers and other additive agents, which are generally used in preparing medicines.

The administration may be either oral administration by tablets, pills, capsules, granules, powders, solutions and the like, or parenteral administration by injections (e.g., intravenous, intramuscular and the like), suppositories, percutaneous preparations, transnasal preparations, inhalations and the like. The dose is optionally decided in response to each case by taking symptoms and age, sex and the like of the object to be administered into consideration, but is generally approximately from 0.001 mg/kg to 100 mg/kg per day per adult in the case of oral administration, and this is administered once or by dividing into 2 to 4 doses. Also, in the case of intravenous administration, it is administered generally once to 2 or more times a day within a range of from 0.0001 mg/kg to 10 mg/kg per once per adult. Also, in the case of transnasal administration, it is administered generally once to 2 or more times a day within a range of from 0.0001 mg/kg to 10 mg/kg per once per adult. In addition, in the case of inhalation, it is administered generally once to 2 or more times a day within a range of from 0.0001 mg/kg to 1 mg/kg per once per adult.

As the solid composition for oral administration by the present invention, tablets, powders, granules and the like are used. In such a solid composition, one or two more active substances are mixed with at least one inert filler such as lactose, mannitol, glucose, hydroxypropylcellulose, microcrystalline cellulose, starch, polyvinyl pyrrolidone, aluminum magnesium silicate or the like. In accordance with the usual way, the composition may contain inert additives such as lubricants (e.g., magnesium stearate and the like), disintegrators (e.g., carboxymethylstarch sodium and the like), stabilizes, and solubilizing agents. As occasion demands, the tablets or pills may be coated with a sugar coating or a gastric or enteric coating.

As the liquid composition for oral administration, pharmaceutically acceptable emulsions, solutions, suspensions, syrups, elixirs and the like are included, which contain generally used inert solvents such as purified water or ethanol. In addition to the inert diluents, this composition may contain auxiliary agents (e.g., solubilizing agents, moistening agents, suspending agents and the like), sweeteners, correctives, aromatics, and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oil (e.g., olive oil or the like), alcohol (e.g., ethanol or the like), polysorbate 80 (name in Pharmacopeia) and the like. Such a composition may further contain tonicity agents, antiseptics, moistening agents, emulsifying agents, dispersing agents, stabilizing agents and solubilizing agents. These are sterilized by, for example, filtration through a bacteria retaining filter, formulation of bactericides or irradiation. In addition, these can also be used by producing a sterile solid composition and dissolving or suspending it in sterile water or a sterile solvent for injection prior to use.

Transmucosal preparations (e.g., inhalations, transnasal preparations and the like) are used in a solid, liquid or semi-solid form and may be produced in accordance with known methods. For example, an excipient such as lactose, starch or the like, as well as a pH adjusting agent, an antiseptic, a surfactant, a lubricant, a stabilizer, a thickener and the like, may be optionally added. An appropriate device for inhalation or blowing may be used for the administration. For example, using a known device or a sprayer (e.g., an inhalation device for measured administration, or the like), a compound may be administered alone or as a powder of a formulated mixture, or as a solution or suspension by a combination with a medicinally acceptable carrier. The dry powder inhaler or the like may be for single or multiple administration use, and a dry powder or a powder-containing capsule may be used. Alternatively, it may be a form such as a pressurized aerosol spray or the like which uses chlorofluoroalkane, hydrofluoroalkane or carbon dioxide or the like suitable gas.

(Test Methods)

Effects of the compound (I) of the present invention were verified by the following pharmacological tests.

Test Method (1) 5-$HT_{2B}$ Receptor Binding Test (i) Preparation of Membrane Sample Cultured human 5-$HT_{2B}$ receptor expressing HEK293-EBNA cells were washed with a phosphate buffer (PBS)(−). The cells were peeled off with a scraper in the presence of PBS(−), and the cells were recovered by centrifugation (1,000 rpm, 10 minutes, 4° C.). In the presence of 5 mM tris-hydrochloric acid (Tris-HCl) (pH 7.4) buffer, homogenized using a homogenizer (registered trademark: Polytron (PTA 10-TS)), and centrifugation-treated (40,000×g, 10 minutes, 4° C.). In the presence of 50 mM Tris-HCl (pH 7.4) buffer, suspended using Glass-Teflon (registered trademark) homogenizer. By carrying out centrifugation treatment (40,000×g, 10 minutes, 4° C.), suspended in 50 mM Tris-HCl (pH 7.4) and stored at −80° C.

(ii) Receptor Binding Test

A total volume of 500 µl containing 50 mM Tris-HCl, a 4 mM $CaCl_2$ (pH 7.4) buffer, a human 5-$HT_{2B}$ receptor expressing HEK293-EBNA cell membrane preparation and a radioligand [$^3$H] Mesulergine (3.1 TBq/mmol) was incubated at 25° C. for 1 hour. The compound was dissolved in 100% dimethyl sulfoxide (DMSO) and diluted to respective concentrations. Binding quantity in the presence of 1 µM ritanserin was regarded as the nonspecific binding, and a result of subtracting the nonspecific binding quantity from the total binding quantity was regarded as the specific binding quantity. After adding 4 ml of 50 mM Tris-HCl buffer (pH 7.4) and filtering under a reduced pressure using a GF/B glass filter, the filter was washed (4 ml×3) with the same buffer. By soaking the glass filter in 5 ml of a liquid scintillator (trade name: Aquasol-2), the radioactivity quantity was measured using a liquid scintillation counter. The concentration of compound which inhibits 50% of the receptor binding, $IC_{50}$ value, was calculated by nonlinear regression analysis using a statistical analysis software (registered trademark: SAS (ver. 6.11)), and the Ki value which shows affinity for the receptor was calculated using the formula of Cheng & Prussoff; $Ki=IC_{50}/(1+[L]/[Kd])$ ([L]: ligand concentration, [Kd]: dissociation constant). The results are shown in the following Table 1. Ex represents example compound number which is described later.

TABLE 1

| Ex | Ki (nM) |
|---|---|
| 2 | 7.7 |
| 52 | 0.48 |
| 98 | 9.6 |
| 142 | 3.7 |
| 153 | 12 |
| 154 | 2.1 |
| 161 | 8.4 |
| 163 | 7.1 |
| 187 | 0.68 |
| 196 | 7.2 |
| 211 | 7.5 |
| 217 | 2.3 |
| 218 | 9.2 |

Test Method (2) 5-$HT_7$ Receptor Binding Test (i) Preparation of Membrane Sample Cultured human 5-$HT_7$ receptor expressing CHO cells were washed with PBS(−). The cells were peeled off with a scraper in the presence of PBS(−), and the cells were recovered by centrifugation (1,000 rpm, 10 minutes, 4° C.). In the presence of 5 mM Tris-HCl (pH 7.4) buffer, homogenized using a homogenizer (registered trademark: Polytron (PTA 10-TS)), and centrifugation-treated (40,000×g, 10 minutes, 4° C.). In the presence of 50 mM Tris-HCl (pH 7.4) buffer, suspended using Glass-Teflon (registered trademark) homogenizer. By carrying out centrifugation treatment (40,000×g, 10 minutes, 4° C.), suspended in 50 mM Tris-HCl (pH 7.4) and stored at −80° C.

(ii) Receptor Binding Test

A total volume of 500 μl containing 50 mM Tris-HCl, a 4 mM $CaCl_2$ (pH 7.4) buffer, a human 5-$HT_7$ receptor expressing CHO cell membrane preparation and a radio-ligand [$^3H$] 5-HT (3.40 TBq/mmol) was incubated at 25° C. for 1 hour. The compound was dissolved in 100% DMSO and diluted to respective concentrations. Binding quantity in the presence of 10 μM metergoline was regarded as the nonspecific binding, and a result of subtracting the nonspecific binding quantity from the total binding quantity was regarded as the specific binding quantity. After adding 4 ml of 50 mM Tris-HCl buffer (pH 7.4) and filtering under a reduced pressure using a GF/B glass filter, the filter was washed (4 ml×3) with the same buffer. By soaking the glass filter in 5 ml of a liquid scintillator (trade name: Aquasol-2), the radioactivity quantity was measured using a liquid scintillation counter. The concentration of compound which inhibits 50% of the receptor binding, $IC_{50}$ value, was calculated by nonlinear regression analysis using SAS (ver. 6.11)), and the Ki value which shows affinity for the receptor was calculated using the formula of Cheng & Prussoff; $Ki=IC_{50}/(1+[L]/[Kd])$ ([L]: ligand concentration, [Kd]: dissociation constant). The results are shown in the following Table 2.

TABLE 2

| Ex | Ki (nM) |
|---|---|
| 2 | 1.1 |
| 52 | 1.3 |
| 98 | 28 |
| 142 | 1.5 |
| 153 | 6.5 |
| 154 | 14 |
| 161 | 5.3 |
| 163 | 4.1 |
| 187 | 11 |
| 196 | 1.8 |
| 211 | 3.1 |
| 217 | 8.2 |
| 218 | 4.3 |

Test Method (3) Affinity for Other Receptors

Affinities for 5-$HT_{1A}$, 5-$HT_{1B}$, 5-$HT_{2A}$, 5-$HT_{2C}$, 5-$HT_3$, 5-$HT_4$, 5-$HT_6$, $\alpha_1$, $M_1$ and $D_2$ receptors may be verified using a known method ("Journal of Neurochemistry" (England), 1986, vol. 47, p. 529-540; "Molecular Pharmacology", (USA), 1982, vol. 21, p. 301-314; "European Journal of Pharmacology", (Holland), 1985, vol. 106, p. 539-546; "The Journal of Pharmacology Experimental Therapeutics", (USA), 1992, vol. 263, p. 1127-1132; "British Journal of Pharmacology", (England), 1993, vol. 109, p. 618-624; "Molecular Pharmacology", (USA), 1993, vol. 43, p. 320-327; "Molecular Pharmacology", (USA), 1989, vol. 35, p. 324-330; "Cellular and Molecular Neurobiology", (Germany), 1988, vol. 8, p. 181-191; or "European Journal of Pharmacology", (Holland), 1988, vol. 173, p. 177-182).

In this connection, affinities of the RS-127445 (2-amino-4-(4-fluoronaphth-1-yl)-6-isopropylpyrimidine; see WO 97/44326 for its production method) and SB-269970 ((R)-3-(2-(2-(4-methylpiperidin-1-yl)ethyl)pyrrolidine-1-sulfonyl) phenol; see International Publication No. 97/48681 for its production method) described in the following test method (4) for respective receptors are known, and regarding the RS-127445, it has been reported for example in "British Journal of Pharmacology", (England), 1999, vol. 127, p. 1075-1082, that said compound has a pKi value of 9.5 for 5-$HT_{2B}$ receptor and is 5-$HT_{2B}$ receptor-selective by a factor of 1000 times or more for the receptors such as 5-$HT_{1A}$, 5-$HT_{1B}$, 5-$HT_{2A}$, 5-$HT_{2C}$, 5-$HT_3$, 5-$HT_6$, 5-$HT_7$, $\alpha_1$, $M_1$, $D_2$ and the like. Also, regarding the SB-269970, it has been reported for example in "Journal of Medicinal Chemistry", (USA), 2000, vol. 43, p. 342-345, that said compound has a pKi value of 8.9 for 5-$HT_{2B}$ receptor and is 5-$HT_7$ receptor-selective by a factor of 250 times or more for the receptors such as 5-$HT_{1A}$, 5-$HT_{1B}$, 5-$HT_{2A}$, 5-$HT_{2B}$, 5-$HT_{2C}$, 5-$HT_4$, 5-$HT_6$, $\alpha_1$, $D_2$ and the like.

Test method (4) Defecation Suppressing Effect at the Time of Restraint Stress Loading The IBS-treating effect of the compound (I) of the present invention was evaluated using a test method in which the amount of excreted faces is measured by loading a restraint stress on rats (see "The Journal of Pharmacology Experimental Therapeutics", (USA), 1992, vol. 261, p. 297-303). This test is an animal model in which it is known that a 5-$HT_3$ receptor antagonist as a diarrhea type IBS-treating agent shows its efficacy.

Test Method

The agent to be tested was administered to male Wistar rats (body weight 250 to 320 g, 10 animals for each group), and a restraint stress was loaded 30 minutes thereafter. A restraint cage (trade name: KN-468, 265 mm in width×95 mm in length×200 mm in height, Natsume Seisakusho, Tokyo) was used for the restraint stress loading, and the number of faces excreted during 1 hour after the stress loading was counted.

As shown in FIG. 1, the RS-127445 as a 5-$HT_{2B}$-selective antagonistic compound did not show defecation-suppressing action even when a dose of 10 mg/kg was orally administered (p.o.).

Figure 2:
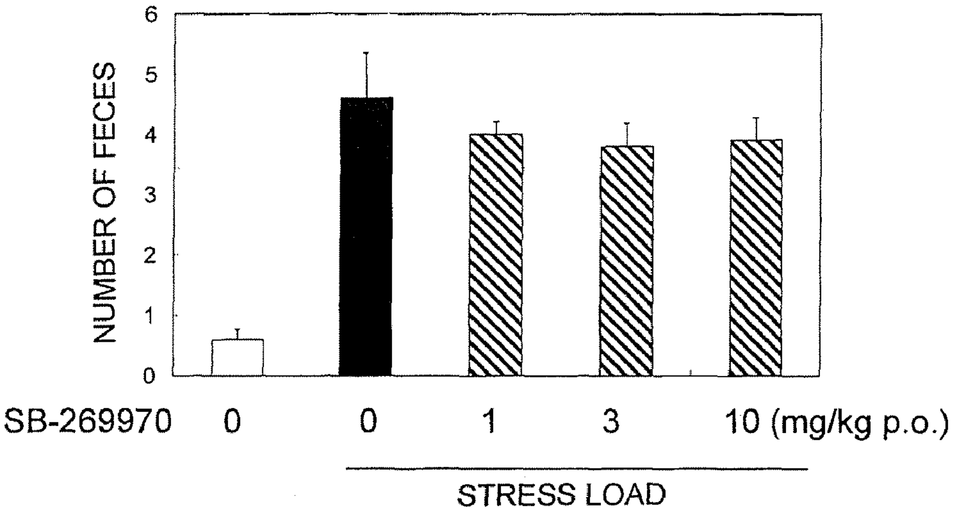
FIG. 2 is a graph showing a result of the measurement of the number of faces excreted at the time of SB-269970 administration, in the rat restraint stress defecation model of the test method (4). Significant difference was not found in the 1, 3 or 10 mg/kg administration group in comparison with the non-administration group (N-10).

In addition, as shown in FIG. 2, the SB-269970 as a 5-$HT_7$-selective antagonistic compound also did not show the defecation-suppressing action even at a dose of 10 mg/kg (p.o.).

Figure 3:
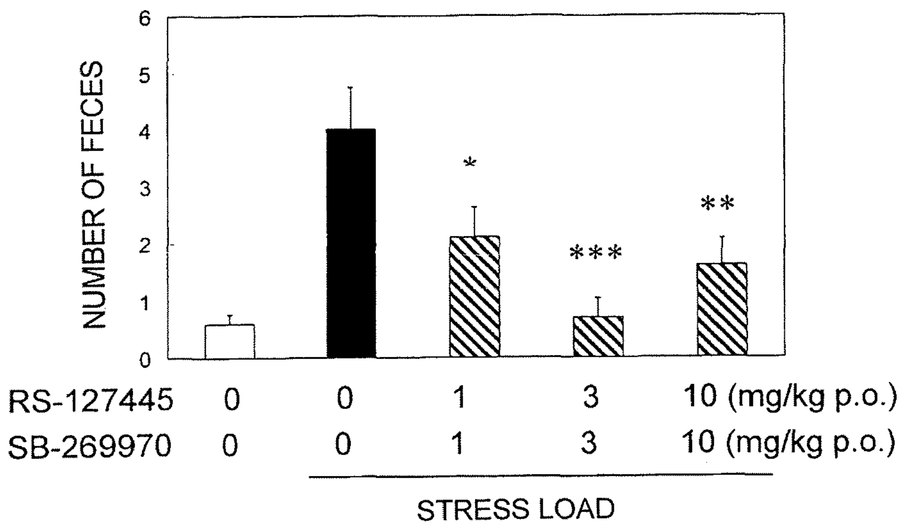
FIG. 3 is a graph showing a result of the measurement of the number of faces excreted at the time of the simultaneous administration of RS-127445 and SB-269970, in the rat restraint stress defecation model of the test method (4). The statistical test was carried out by the Dunnett's method, and * shows a level of significance of 5%, and  that of 1% and * that of 0.1% (N=10).

On the other hand, as shown in FIG. 3, it was revealed that a synergistic effect may be obtained when both of the compounds RS-127445 and SB-269970 are simultaneously administered. That is, as shown in FIG. 1 and FIG. 2, each of the RS-127445 and SB-269970 alone did not show the action even at 10 mg/kg (p.o.), but when both compounds were simultaneously administered, it was revealed that they show a significant suppressive action starting from a dose of 1 mg/kg (p.o.).

Based on the above results, it is expected that when the compound of the present invention possesses the 5-$HT_{2B}$ receptor antagonism together with the 5-$HT_7$ receptor antagonism, it will show a superior IBS morbid state-improving effect in comparison with the selective receptor antagonists against one of the receptors.

This effect was the same when a compound of the present invention having both of the 5-$HT_{2B}$ receptor antagonism and 5-$HT_7$ receptor antagonism was used.

Figure 4:
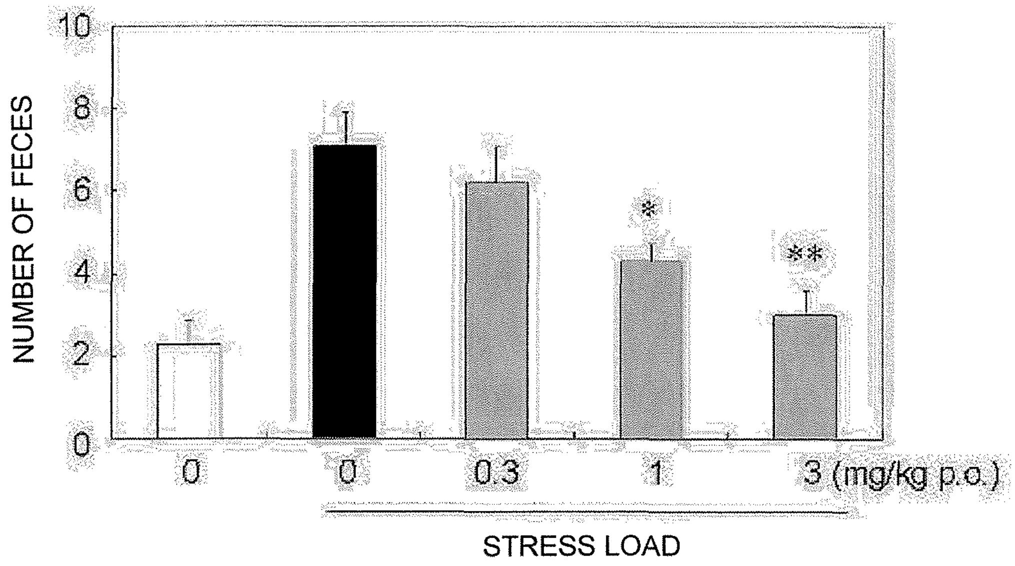
FIG. 4 is a graph showing a result of the measurement of the number of faces excreted at the time of the administration of the Example compound 161, in the rat restraint stress defecation model of the test method (4). The statistical test was carried out by the Dunnett's method, and * shows a level of significance of 5%, and ** that of 1% (N=10).

As shown in FIG. 4, when the Example compound 161 was administered, it showed a significant suppressing action starting from a dose of 1 mg/kg (p.o.).

Figure 5:
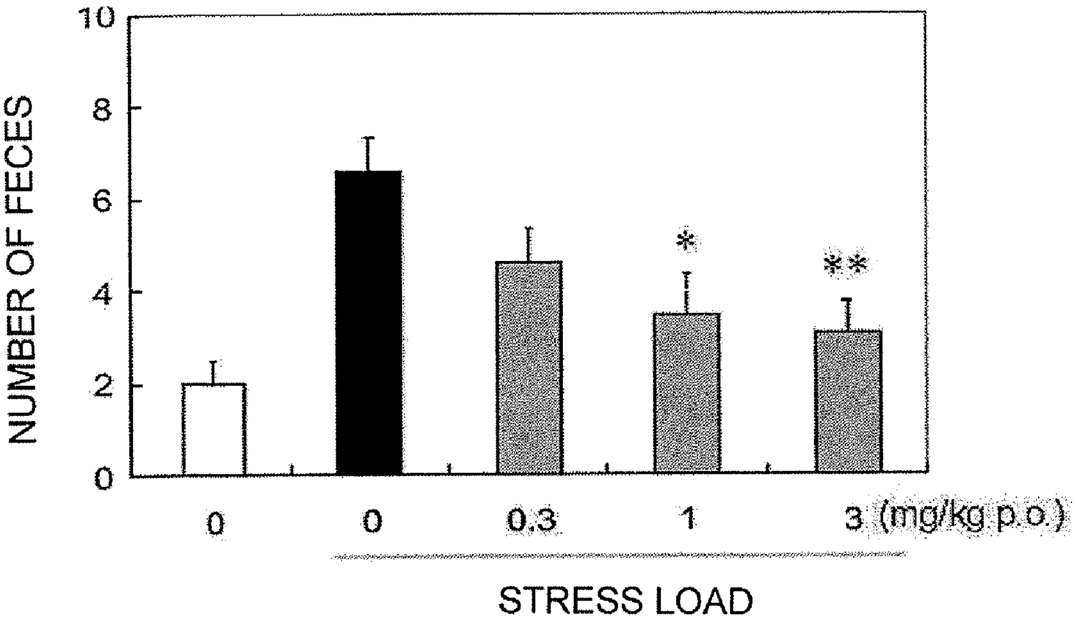
FIG. 5 is a graph showing a result of the measurement of the number of faces excreted at the time of the administration of the Example compound 153, in the rat restraint stress defecation model of the test method (4). The statistical test was carried out by the Dunnett's method, and * shows a level of significance of 5%, and ** that of 1% (N=10).

As shown in FIG. 5, when the Example compound 153 was administered, it showed a significant suppressing action starting from a dose of 1 mg/kg (p.o.).

Figure 6:
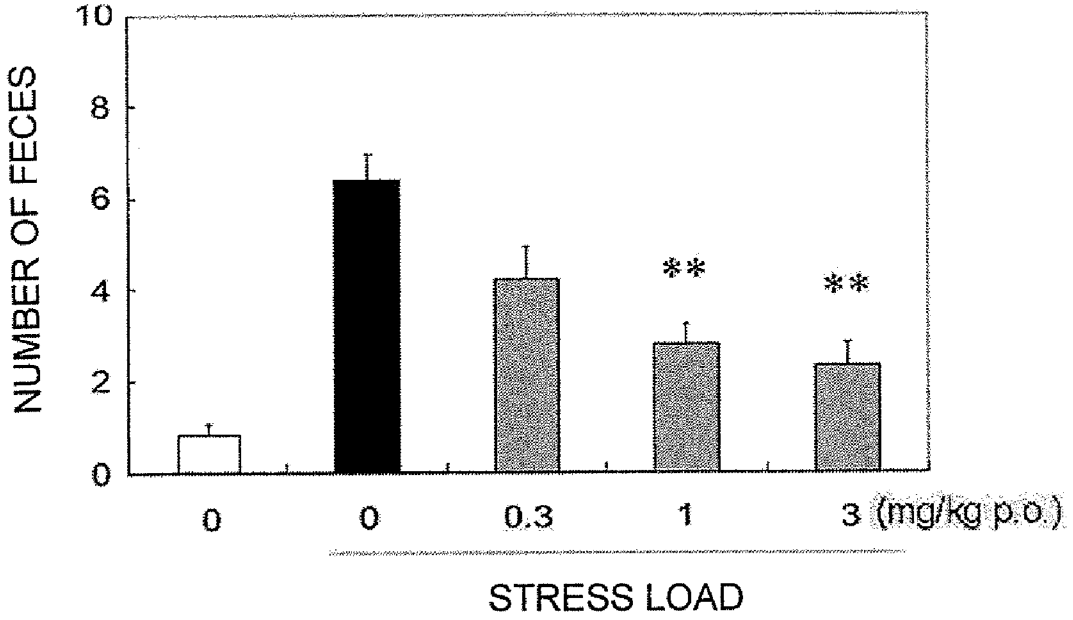
FIG. 6 is a graph showing a result of the measurement of the number of faces excreted at the time of the administration of the Example compound 154, in the rat restraint stress defecation model of the test method (4). The statistical test was carried out by the Dunnett's method, and ** shows a level of significance of 1% (N=10).

As shown in FIG. 6, when the Example compound 154 was administered, it showed a significant suppressing action starting from a dose of 1 mg/kg (p.o.).

As a result of the aforementioned each test, the 5-$HT_{2B}$ receptor antagonism and 5-$HT_7$ receptor antagonism were confirmed, and based on this, the usefulness as a therapeutic agent for IBS and a preventive agent for migraine is evident.

EXAMPLES

The following illustratively describes production methods of the compounds of the present invention with reference to the production examples of the compounds of the present invention, but the present invention is not restricted by these examples. In this connection, since novel compounds are included in the starting compounds of the compounds of the present invention, production methods of these compounds are described as production examples.

In this connection, symbols in the production examples and Example represent the following meanings (the same shall apply hereinafter).

REx: production example number, Ex: Example number, No: compound number, Str: structural formula, Dat: physical data (FAB: FAB-MS (POS) ($M^+$+1 unless otherwise noted), FN: FAB-MS (NEG) ($M^{-1}$−1 unless otherwise noted), ESI: ESI-MS (POS) ($M^+$+1 unless otherwise noted); NMR: δ (ppm) of characteristic peak in $^1$H-NMR), Sal: salt (Oxa: oxalate, Fum: fumarate, a blank space or no description indicates that it is a free form, and the numeral before the acid component indicates molar ratio; for example, 2HCl is described, it shows that the compound is dihydrochloride), Me: methyl, Et: ethyl, nPr: normal propyl, iPr: isopropyl, cPr: cyclopropyl, nBu: normal butyl, iBu: isobutyl, tBu: tert-butyl, cBu: cyclobutyl, cPen: cyclopentyl, cHex: cyclohexyl, cHep: cycloheptyl, cOct: cyclooctyl, Ph: phenyl, Bn: benzyl, null: no substitution; the numeral before the substituent group indicates its substitution position, and for example, 5-F means 5-fluoro; and RSyn and Syn: production method (the numerals indicate that they were produced using the corresponding starting materials similar to the case of compounds respectively having the numerals as the production example numbers or Example numbers).

Production Example 1

A 6.214 g portion of sodium hydride (55% dispersion in oil) was washed with hexane, 150 ml of tetrahydrofuran was added thereto and, under ice-cooling, a solution prepared by dissolving 18.534 g of ethyl 3-oxobutanoate in 75 ml of tetrahydrofuran was added dropwise thereto. After stirring at room temperature for 30 minutes, this solution was added dropwise, under ice-cooling, to a solution prepared by dissolving 25.500 g of 1-bromo-3,3-dimethyl-2-butanone in 150 ml of tetrahydrofuran, followed by stirring overnight at room temperature. After adding 171 ml of 1 M hydrochloric acid to the reaction liquid, tetrahydrofuran was evaporated under a reduced pressure. The residue was extracted with diethyl ether, and the organic layer was washed with water (twice) and saturated brine and then dried over anhydrous sodium sulfate. By evaporating the solvent under a reduced pressure, 30.51 g of ethyl 2-acetyl-5,5-dimethyl-4-oxohexanoate was obtained as yellow oil. A 15.00 g portion of this product was dissolved in 250 ml of acetic acid, and 9.48 ml of 4-fluorophenethylamine was added thereto, followed by stirring at 100° C. for 4 hours. The solvent was evaporated under a reduced pressure. The residue was dissolved in ethyl acetate and washed with water, a 1 M sodium hydroxide aqueous solution (twice) and saturated brine. After drying with anhydrous sodium sulfate, the solvent was evaporated under a reduced pressure, and the residue was purified by silica gel column chromatography (ethyl acetate:hexane=1:15-1:10) to obtain 15.91 g of ethyl 5-tert-butyl-1-[2-(4-fluorophenyl) ethyl]-2-methyl-1H-pyrrole-3-carboxylate as a colorless solid.

Production Example 2

A 2.987 g portion of ethyl 5-cyclohexyl-1-[2-(4-fluorophenyl)ethyl]-2-methyl-1H-pyrrole-3-carboxylate was dissolved in 16 ml of ethanol, and 13.37 ml of a 5 M sodium hydroxide aqueous solution was added thereto, followed by stirring at 80° C. for 40 hours. The reaction liquid was concentrated under a reduced pressure, and water was added to the residue. After washing with diethyl ether, 37% hydrochloric acid was added thereto until pH became 1. The resulting solid was collected by filtration and washed with water to obtain 1.859 g of 5-cyclohexyl-1-[2-(4-fluorophenyl)ethyl]-2-methyl-1H-pyrrole-3-carboxylic acid as a light brown solid.

Production Example 3

A 15.91 g portion of ethyl 5-tert-butyl-1-[2-(4-fluorophenyl)ethyl]-2-methyl-1H-pyrrole-3-carboxylate was dissolved in a mixture of 200 ml of ethanol and 20 ml of tetrahydrofuran at 80° C., and 96.01 ml of a 5 M sodium hydroxide aqueous solution was added thereto, followed by overnight stirring at the same temperature and then further stirring at 100° C. for 6 hours. The reaction liquid was concentrated to about 150 ml, and, under ice-cooling, 6 M hydrochloric acid was added thereto until pH became 1. The resulting solid was collected by filtration and washed with water to obtain 14.04 g of 5-tert-butyl-1-[2-(4-fluorophenyl)ethyl]-2-methyl-1H-pyrrole-3-carboxylic acid as a light brown solid.

Production Example 4

A 340 mg portion of benzyl 4-{4-(tert-butoxycarbonyl)-1-[2-(4-fluorophenyl)ethyl]-5-methyl-1H-pyrrol-2-yl}piperidine-1-carboxylate was dissolved in 7 ml of methanol, and 159 μl of 37% formalin, 3 drops of acetic acid and 45 mg of 10% palladium-activated carbon were added, followed by stirring at room temperature for 2 hours in an atmosphere of hydrogen. The reaction liquid was filtered through celite, the filtrate was concentrated under a reduced pressure, 50 ml of a saturated sodium bicarbonate aqueous solution was added to the residue, and the resulting solid was collected by filtration to obtain 232 mg of tert-butyl 1-[2-(4-fluorophenyl) ethyl]-2-methyl-5-(1-methylpiperidin-4-yl)-1H-pyrrole-3-carboxylate as a colorless solid.

Production Example 5

A 230 mg portion of tert-butyl 1-[2-(4-fluorophenyl) ethyl]-2-methyl-5-(1-methylpiperidin-4-yl)-1H-pyrrole-3-carboxylate was dissolved in 2 ml of dichloromethane, and 1 ml of trifluoroacetic acid was added under ice-cooling, followed by stirring at room temperature for 1.5 hours. The reaction liquid was concentrated under a reduced pressure, and a saturated sodium bicarbonate aqueous solution was added, followed by three times extractions with chloroform. After drying the organic layer with anhydrous sodium sulfate, the solvent was evaporated under a reduced pressure, and the residue was purified by silica gel column chromatography (methanol:chloroform=10:90-15:85-20:80) to obtain 124 mg of 1-[2-(4-fluorophenyl)ethyl]-2-methyl-5-(1-methylpiperidin-4-yl)-1H-pyrrole-3-carboxylic acid as a colorless solid.

Production Example 6

A 266 mg portion of 2-methyl-5-(trifluoromethyl)-1H-pyrrole-3-carbonitrile was dissolved in 10 ml of toluene, and 0.382 ml of 2-(4-fluorophenyl)ethanol and 352 mg of cyanomethylenetrimethylphospholan were added, followed by stirring at 100° C. for 1.5 hours. The reaction liquid was concentrated under a reduced pressure, and the resulting residue was purified by silica gel column chromatography (ethyl acetate:hexane=1:9-1:4) to obtain 451 mg of 1-[2-(4-fluorophenyl)ethyl]-2-methyl-5-(trifluoromethyl)-1H-pyrrole-3-carbonitrile as a white solid.

Production Example 7

A 1.364 g portion of benzyl 5-[3-(1,3-dioxo-1,3-dihydro-2H-isoindol-2-yl)propyl]-1-[2-(4-fluorophenyl)ethyl]-2-methyl-1H-pyrrole-3-carboxylate was dissolved in a mixed solvent of 10 ml ethanol and 10 ml tetrahydrofuran, and 0.139 ml of hydrazine monohydrate was added, followed by stirring at room temperature for 24 hours. Then, 0.252 ml of hydrazine monohydrate was added, followed by stirring at 50° C. for 5 hours. Further, 0.252 ml of hydrazine monohydrate was added, followed by stirring at 50° C. for 20 hours. The reaction liquid was cooled to room temperature and then filtered through celite. The filtrate was concentrated under a reduced pressure, chloroform was added to the residue, and the resulting precipitate was removed by celite-filtration. The filtrate was concentrated under a reduced pressure, and the residue was purified by silica gel column chromatography (Chromatorex (registered trademark), ethyl acetate) to obtain 850 mg of benzyl 5-(3-aminopropyl)-1-[2-(4-fluorophenyl)ethyl]-2-methyl-1H-pyrrole-3-carboxylate as a colorless oil.

Production Example 8

A 568 mg portion of benzyl 5-(3-aminopropyl)-1-[2-(4-fluorophenyl)ethyl]-2-methyl-1H-pyrrole-3-carboxylate was dissolved in 7 ml of tetrahydrofuran, 0.245 ml of 37% formalin was added, and then 964 mg of sodium triacetoxyborohydride was added under ice-cooling, followed by stirring at room temperature for 15 hours. A saturated sodium bicarbonate aqueous solution was added to the reaction solution, followed by extraction with ethyl acetate. The organic layer was washed with saturated brine and dried over anhydrous sodium sulfate. The solvent was evaporated under a reduced pressure, and the residue was purified by silica gel column chromatography (methanol:chloroform=2:98-15:85) to obtain 503 mg of benzyl 5-[3-(dimethylamino)propyl]-1-[2-(4-fluorophenyl)ethyl]-2-methyl-1H-pyrrole-3-carboxylate as a colorless oil.

Production Example 9

A 501 mg portion of benzyl 5-[3-(dimethylamino)propyl]-1-[2-(4-fluorophenyl)ethyl]-2-methyl-1H-pyrrole-3-carboxylate was dissolved in a mixed solvent of 1 ml ethanol and 5 ml tetrahydrofuran, and 119 mg of 10% palladium-activated carbon was added, followed by stirring at room temperature for 15 hours under an atmosphere of hydrogen. The reaction liquid was filtered through celite, and the filtrate was concentrated under a reduced pressure. The residue was purified by silica gel column chromatography (methanol:chloroform=10:90-15:85-20:80), to obtain 342 mg of 5-[3-(dimethylamino)propyl]-1-[2-(4-fluorophenyl)ethyl]-2-methyl-1H-pyrrole-3-carboxylic acid as a colorless solid.

Production Example 10

A 6.00 g portion of benzyl 2-acetyl-4-oxo-4-phenylbutanoate was dissolved in a mixture of 54 ml acetic acid and 5.4 ml water, and 14.9 g of ammonium acetate was added, followed by stirring at 100° C. for 1 hour. After evaporation of the solvent under a reduced pressure and subsequent addition of ethyl acetate-water, the ethyl acetate layer was washed with a 1 M sodium hydroxide aqueous solution and saturated brine, followed by drying with anhydrous sodium sulfate. Then, the solvent was evaporated under a reduced pressure. The residue was purified by silica gel column chromatography (ethyl acetate:hexane=1:5-1:4) to obtain 3.84 g of benzyl 2-methyl-5-phenyl-1H-pyrrole-3-carboxylate as a light purple solid.

Production Example 11

A 500 mg portion of benzyl 2-methyl-5-phenyl-1H-pyrrole-3-carboxylate was dissolved in 10 ml of tetrahydrofuran, and 79 mg of sodium hydride (55% dispersion in oil) was added under ice-cooling, followed by stirring at room temperature for 30 minutes. A 0.357 ml portion of benzyl chloromethyl ether was added dropwise to this solution under ice-cooling, followed by stirring at room temperature for 1.5 hours. After adding water under ice-cooling, extraction was carried out with ethyl acetate. Then, after washing with saturated brine and then drying with anhydrous sodium sulfate, the solvent was evaporated under a reduced pressure. The residue was purified by silica gel column chromatography (ethyl acetate:hexane=1:10-1:8) to obtain 503 mg of benzyl 1-[(benzyloxy)methyl]-2-methyl-5-phenyl-1H-pyrrole-3-carboxylate as a colorless liquid.

Production Example 12

Under ice-cooling, 0.72 ml of phosphorus oxychloride was added to 4 ml of N,N-dimethylformamide at an inner temperature of from 10 to 20° C., followed by stirring at room temperature for 15 minutes. A 5 ml portion of N,N-dimethylformamide solution of 2.00 g ethyl 5-tert-butyl-2-methyl-1-(2-phenylethyl)-1H-pyrrole-3-carboxylate was added to this solution under ice-cooling at an inner temperature of from 10 to 20° C., followed by stirring overnight at 60° C. Water was added at 0° C., pH was adjusted to 8 with potassium carbonate, and extraction was carried out with diethyl ether. The organic layer was washed with water and saturated brine and dried over anhydrous sodium sulfate. Then, the solvent was evaporated under a reduced pressure. The residue was purified by silica gel column chromatography (ethyl acetate:hexane=1:10-1:8-1:7) to obtain 1.63 g of ethyl 5-tert-butyl-4-formyl-2-methyl-1-(2-phenylethyl)-1H-pyrrole-3-carboxylate as a light yellow solid.

Production Example 13

A 700 mg portion of ethyl 5-tert-butyl-4-formyl-2-methyl-1-(2-phenylethyl)-1H-pyrrole-3-carboxylate was dissolved in 21 ml of trifluoroacetic acid, mixed with 3.3 ml of triethylsilane at 0° C. and stirred for 2 hours while rising the temperature from 0° C. to room temperature. The solvent was evaporated under a reduced pressure, azeotropy with toluene was carried out, and then the residue was purified by silica gel column chromatography (ethyl acetate:hexane=1:50-1:40-1:30) to obtain 652 mg of ethyl 5-tert-butyl-2,4-dimethyl-1-(2-phenylethyl)-1H-pyrrole-3-carboxylate as a colorless oil.

Production Example 14

A 300 mg portion of ethyl 5-tert-butyl-2-methyl-1-(2-phenylethyl)-1H-pyrrole-3-carboxylate was suspended in 9 ml of ethanol, and 1.8 ml of a 8 M potassium hydroxide aqueous solution was added, followed by stirring overnight at 100° C. The reaction liquid was cooled to room temperature, adjusted to pH 1 by adding 6 M hydrochloric acid and 1 M hydrochloric acid under ice-cooling, and then stirred at the same temperature for 1 hour. The resulting solid was collected by filtration, washed with water and then dried at 90° C. under a reduced pressure to obtain 269 mg of 5-tert-butyl-2-methyl-1-(2-phenylethyl)-1H-pyrrole-3-carboxylic acid as a colorless solid.

Production Example 15

A 750 mg portion of ethyl 5-tert-butyl-1-[2-(4-fluorophenyl)ethyl]-4-formyl-2-methyl-1H-pyrrole-3-carboxylate was suspended in 15 ml of ethanol, and 158 mg of sodium borohydride was added at 0° C., followed by stirring at room temperature for 2 hours. The solvent was evaporated under a reduced pressure, chloroform and water were added, and the organic layer was washed with saturated brine and then dried over anhydrous sodium sulfate. By evaporating the solvent under a reduced pressure, 754 mg of ethyl 5-tert-butyl-1-[2-(4-fluorophenyl)ethyl]-4-(hydroxymethyl)-2-methyl-1H-pyrrole-3-carboxylate was obtained as a colorless solid.

Production Example 16

A 719 mg portion of ethyl 5-tert-butyl-1-[2-(4-fluorophenyl)ethyl]-4-(hydroxymethyl)-2-methyl-1H-pyrrole-3-carboxylate was suspended in 10 ml of ethanol, and 2.0 ml of 4 M hydrogen chloride/1,4-dioxane was added, followed by stirring overnight at room temperature. By adding 10 ml of a 1 M sodium hydroxide aqueous solution, ethanol was evaporated under a reduced pressure. After extraction with ethyl acetate, the organic layer was washed with saturated brine and dried over anhydrous sodium sulfate. After evaporation of the solvent under a reduced pressure, the residue was purified by silica gel column chromatography (Chromatorex (registered trademark), ethyl acetate:hexane=1:30-1:20-1:15) to obtain 623 mg of ethyl 5-tert-butyl-4-(ethoxymethyl)-1-[2-(4-fluorophenyl)ethyl]-2-methyl-1H-pyrrole-3-carboxylate as a colorless oil.

Production Example 17

Bioorganic & Medicinal Chem. Lett., 14 (2004), 1295-1298, was used as a reference. A 1.00 g portion of ethyl 5-tert-butyl-1-[2-(4-fluorophenyl)ethyl]-2-methyl-1H-pyrrole-3-carboxylate was dissolved in 15 ml of toluene, 0.26 ml of acetyl chloride was added thereto, and 3.6 ml of tin(IV) chloride (a 1 M dichloromethane solution) was added dropwise thereto at 0° C., followed by stirring at room temperature for 6 hours. After adjusting to pH 12 by adding 25 ml of a 1 M sodium hydroxide aqueous solution at 0° C., extraction was carried out with ethyl acetate, followed by washing with saturated brine. After drying with anhydrous sodium sulfate, the solvent was evaporated under a reduced pressure, and the residue was purified by silica gel column chromatography (ethyl acetate:hexane=1:10-1:7-1:5) to obtain 668 mg of ethyl 5-acetyl-1-[2-(4-fluorophenyl)ethyl]-2-methyl-1H-pyrrole-3-carboxylate as a beige solid.

Production Example 18

A 1.035 g portion of (methoxymethyl)triphenyl-phosphonium chloride was suspended in 5 ml of tetrahydrofuran, and 339 mg of potassium tert-butoxide was added thereto at 0° C. After 15 minutes of stirring at 0° C. and subsequent cooling to −78° C., 500 mg of ethyl 5-ethyl-1-[2-(4-fluorophenyl)ethyl]-4-formyl-2-methyl-1H-pyrrole-3-carboxylate was added thereto, followed by gradual warming to 0° C. Extraction with ethyl acetate was carried out by adding water at 0° C., followed by washing with water and saturated brine in that order and subsequent drying with anhydrous sodium sulfate. After evaporation of the solvent under a reduced pressure, the residue was purified by silica gel column chromatography (ethyl acetate:hexane=1:10-1:7) to obtain 313 mg of a light green oily product. A 313 mg portion of this product was dissolved in 10 ml of ethanol, and 30 mg of 10% palladium-activated carbon was added, followed by stirring at room temperature for 5 hours under an atmosphere of hydrogen. After celite filtration, the solvent was evaporated under a reduced pressure to obtain 293 mg f ethyl 5-ethyl-1-[2-(4-fluorophenyl)ethyl]-4-(2-methoxyethyl)-2-methyl-1H-pyrrole-3-carboxylate as a colorless solid.

In the same manner as the methods of the above-mentioned Production Examples 1 to 18, Production Example compounds 19 to 86 shown in Tables 3 to 10 which are described later were produced using respectively corresponding starting materials. Structures and physical data of the Production Example compounds are shown in Tables 3 to 10 which are described later.

Example 1

A 555 mg portion of 5-cyclohexyl-1-[2-(4-fluorophenyl)ethyl]-2-methyl-1H-pyrrole-3-carboxylic acid was dissolved in 10 ml of N,N-dimethylformamide, and 410 mg of 1,1'-carbonyldiimidazole was added under ice-cooling, followed by stirring at 70° C. for 1.5 hours. A 759 mg portion of guanidine carbonate was added to this reaction liquid, followed by stirring at 50° C. for 15 hours. Water was added to the reaction solution, followed by extraction with ethyl acetate. The organic layer was washed with saturated brine, and then the solvent was evaporated under a reduced pressure. After purifying the residue by silica gel column chromatography (Chromatorex (registered trademark), methanol/chloroform=2:98-10:90), the resulting product was dissolved in 5 ml of ethyl acetate, and 0.320 ml of 4 M hydrogen chloride/ethyl acetate was added under ice-cooling, followed by stirring overnight at room temperature. Then, the solid formed by adding diethyl ether was collected by filtration to obtain 323 mg of 5-cyclohexyl-N-(diaminomethylene)-1-[2-(4-fluorophenyl)ethyl]-2-methyl-1H-pyrrole-3-carboxamide hydrochloride as a white solid.

Example 2

A 910 mg portion of 5-tert-butyl-1-[2-(4-fluorophenyl)ethyl]-2-methyl-1H-pyrrole-3-carboxylic acid was dissolved in 10 ml of N,N-dimethylformamide, and under ice-cooling 748 mg of 1-ethyl-3-(3-dimethylaminopropyl)carbodiimide hydrochloride and 527 mg of 1-hydroxybenzotriazole were added, followed by stirring at the same temperature for 1 hour. A 0.65 ml portion of N,N-dimethylethane-1,2-diamine was added to the reaction liquid, and after stirring at room temperature for 15 hours, the solvent was evaporated under a reduced pressure. Ethyl acetate was added to the residue and, after washing with a saturated sodium bicarbonate aqueous solution, water and saturated brine, the organic layer was dried over anhydrous magnesium sulfate. After evaporation of the solvent under a reduced pressure, the residue was washed with ethyl acetate to obtain 783 mg of 5-tert-butyl-N-[2-(dimethylamino)ethyl]-1-[2-(4-fluorophenyl)ethyl]-2-methyl-1H-pyrrole-3-carboxamide as a colorless solid. A 783 mg portion of this product was dissolved in 5 ml of methanol, and 1 ml of 4 M hydrogen chloride/ethyl acetate was added under ice-cooling, followed by stirring at the same temperature for 30 minutes. The solvent was evaporated under a reduced pressure, and the resulting residue was solidified with methanol-ethyl acetate to obtain 360 mg of 5-tert-butyl-N-[2-(dimethylamino)ethyl]-1-[2-(4-fluorophenyl)ethyl]-2-methyl-1H-pyrrole-3-carboxamide as a colorless solid.

Example 3

A 330 mg portion of 5-tert-butyl-N-(diaminomethylene)-1-[2-(2-methoxyphenyl)ethyl]-2-methyl-1H-pyrrole-3-carboxamide was dissolved in 10 ml of dichloromethane, and 2.78 ml of a 1 M boron tribromide dichloromethane solution was added dropwise thereto at −70° C. under an atmosphere of argon, followed by stirring at room temperature for 14 hours. Under ice-cooling, 5 ml of methanol was added to the reaction liquid, and the reaction liquid was concentrated under a reduced pressure. The residue was subjected to three times of azeotropy with methanol, and a saturated sodium bicarbonate aqueous solution and saturated brine were added to the residue, followed by extraction with 20% methanol/chloroform. After drying the organic layer with anhydrous sodium sulfate, the solvent was evaporated under a reduced pressure, and the residue was purified by silica gel column chromatography (Chromatorex (registered trademark), methanol:chloroform=10:90). The resulting product was dissolved in 3 ml of ethanol and, under ice-cooling, 0.263 ml of 4 M hydrogen chloride/ethyl acetate was added, followed by stirring at room temperature for 15 hours. Then, the solid formed by adding ethyl acetate was collected by filtration to obtain 206 mg of 5-tert-butyl-N-(diaminomethylene)-1-[2-(2-hydroxyphenyl)ethyl]-2-methyl-1H-pyrrole-3-carboxamide hydrochloride as a light brown solid.

Example 4

A 230 mg portion of benzyl 4-{4-{[(diaminomethylene)amino]carbonyl}-1-[2-(4-fluorophenyl)ethyl]-5-methyl-1H-pyrrol-2-yl}piperidine-1-carboxylate was dissolved in 5 ml of ethanol, 45 mg of 10% palladium-activated carbon was added, followed by stirring at room temperature for 5 hours under an atmosphere of hydrogen. After adding chloroform to the reaction liquid, the insoluble matter was separated by celite filtration, and the filtrate was concentrated under a reduced pressure. The residue was purified by silica gel column chromatography (Chromatorex (registered trademark), methanol:chloroform=10:90). The resulting product was dissolved in 3 ml of ethanol, and 0.269 ml of 4 M hydrogen chloride/ethyl acetate was added under ice-cooling, followed by stirring overnight at room temperature. The resulting solid was collected by filtration to obtain 95 mg of N-(diaminomethylene)-1-[2-(4-fluorophenyl)ethyl]-2-methyl-5-piperidin-4-yl-1H-pyrrole-3-carboxamide dihydrochloride as a white solid.

Example 5

A 400 mg portion of N-(diaminomethylene)-1-[2-(4-fluorophenyl)ethyl]-5-(2-methoxyphenyl)-2-methyl-1H-pyrrole-3-carboxamide was dissolved in 10 ml of dichloromethane, and 3.04 ml of a 1 M boron tribromide dichloromethane solution was added dropwise thereto at −70° C. under an atmosphere of argon, followed by stirring at room temperature for 15 hours. Then, 100 ml of a saturated sodium bicarbonate aqueous solution was added to the reaction solution, followed by three times extractions with 20% methanol/chloroform. After drying the organic layer with anhydrous magnesium sulfate, the solvent was evaporated under a reduced pressure, and the residue was purified by silica gel column chromatography (Chromatorex (registered trademark), methanol:chloroform=10:90-20:80). Then, the resulting product was dissolved in 3 ml of ethyl acetate and, under ice-cooling, 0.132 ml of 4 M hydrogen chloride/ethyl acetate was added, followed by stirring overnight at room temperature. The resulting solid was collected by filtration to obtain 90 mg of N-(diaminomethylene)-1-[2-(4-fluorophenyl)ethyl]-5-(2-hydroxyphenyl)-2-methyl-1H-pyrrole-3-carboxamide hydrochloride as a white solid.

Example 6

A 400 mg portion of 5-tert-butyl-N-{[4-(dimethylamino)tetrahydro-2H-thiopyran-4-yl]methyl}-1-[2-(4-fluorophenyl)ethyl]-2-methyl-1H-pyrrole-3-carboxamide was dissolved in 4 ml of chloroform and, under ice-cooling, 210 mg of 3-chloroperbenzoic acid was added, followed by stirring under ice-cooling for 1 hour. Then, 100 mg of 3-chloroperbenzoic acid was added, followed by stirring for 30 minutes. A 10% sodium hydrogen sulfite aqueous solution and a saturated sodium bicarbonate aqueous solution to the reaction solution, followed by extraction with chloroform. The organic layer was washed with saturated brine and dried over anhydrous sodium sulfate. After evaporation of the solvent under a reduced pressure, the residue was purified by silica gel column chromatography (chloroform:methanol:hexane=1:0:0-100:1:0-50:1:0-30:1:0) to obtain 213 mg of 5-tert-butyl-N-{[4-(dimethylamino)-1-oxidotetrahydro-2H-thiopyran-4-yl]methyl}-1-[2-(4-fluorophenyl)ethyl]-2-methyl-1H-pyrrole-3-carboxamide as a colorless oil. This product was dissolved in 2.5 ml of acetonitrile at 80° C., 44 mg of oxalic acid was added, followed by stirring at the same temperature for 10 minutes and then stirring at room temperature for 2 hours. The resulting solid was collected by filtration and then washed with acetonitrile to obtain 199 mg of 5-tert-butyl-N-{[4-(dimethylamino)-1-oxidotetrahydro-2H-thiopyran-4-yl]methyl}-1-[2-(4-fluorophenyl)ethyl]-2-methyl-1H-pyrrole-3-carboxamide oxalate as a colorless solid.

Example 7

A 21.7 mg portion of 2-bromo-1-(3-fluorophenyl)ethanone and 13.9 mg of methyl 3-oxobutanoate were dissolved in 1.0 ml of acetonitrile, and 115 mg of a 1,5,7-triazabicyclo[4.4.0]dec-5-ene-carrying resin (trade name: 1,5,7-Triazabicyclo[4.4.0]dec-5-ene bond to polystyrene crosslinked with 2% DBV, Fluka, Switzerland) was added, followed by stirring at room temperature for 3 hours. Then, the reaction liquid was filtered. By concentrating the filtrate under a reduced pressure, methyl 2-acetyl-4-(3-fluorophenyl)-4-oxobutanoate was obtained as a crude product. A 0.500 ml acetic acid solution of 21.1 mg of 4-fluorophenethylamine hydrochloride was added to the resulting crude product, followed by stirring overnight at 100° C. By evaporating the solvent under a reduced pressure, methyl 5-(3-fluorophenyl)-1-[2-(4-fluorophenyl)ethyl]-2-methyl-1H-pyrrole-3-carboxylate was obtained as a crude product. The resulting crude product was dissolved in a mixed solvent of 0.500 ml tetrahydrofuran and 0.500 ml methanol, and 0.500 ml of a 2 M sodium hydroxide aqueous solution was added, followed by stirring overnight at 60° C. By adding 1 M hydrochloric acid to the reaction liquid at room temperature, the water layer was acidified, followed by extraction with chloroform. By evaporating the solvent of the organic layer under a reduced pressure, 5-(3-fluorophenyl)-1-[2-(4-fluorophenyl)ethyl]-2-methyl-1H-pyrrole-3-carboxylic acid was obtained as a crude product. A 0.600 ml portion of a N,N-dimethylformamide solution of 24 mg 1,1'-carbonylbis-1H-imidazole was added to the resulting crude product and stirred at 50° C. for 2 hours. A solution prepared by adding 5.3 mg of guanidine hydrochloride to 0.400 ml N,N-dimethylformamide solution of 20 mg of sodium hydride (60% dispersion in oil) and stirring at room temperature for 30 minutes was added to this reaction liquid at room temperature, followed by stirring overnight at room temperature. The solvent was evaporated under a reduced pressure, and water was added to the residue, followed by extraction with chloroform. The solvent of the organic layer was evaporated under a reduced pressure, and the resulting residue was purified by a fractional high performance liquid chromatography (acetonitrile/a 0.1% trifluoroacetic acid aqueous solution) to obtain 3.7 mg of N-(diaminomethylene)-5-(3-fluorophenyl)-1-[2-(4-fluorophenyl)ethyl]-2-methyl-1H-pyrrole-3-carboxamide.

Example 8

A 9.1 mg portion of 5-tert-butyl-1-[2-(4-fluorophenyl)ethyl]-2-methyl-1H-pyrrole-3-carboxylic acid, which may be obtained during a production process similar to Example 7 using respectively corresponding starting materials, 5.1 mg of $N^1$,$N^1$-dimethylpropane-1,2-diamine and 4.1 mg of 1-hydroxybenzotriazole, were dissolved in 1.0 ml of N,N-dimethylformamide, and PS-Carbodiimide (Argonaut Technologies, Inc., USA) was added, followed by stirring overnight at room temperature. A 50 mg portion of MP-Carbonate (Argonaut Technologies, Inc., USA) and 50 mg of PS-Isocyanate (Argonaut Technologies, Inc., USA) were added to the reaction liquid at room temperature, followed by stirring for 4 hours. The reaction liquid was filtered, the filtrate was concentrated under a reduced pressure, and the resulting residue was purified by a fractional high performance liquid chromatography (methanol/a 0.1% formic acid aqueous solution) to obtain 1.5 mg of 5-tert-butyl-N-[2-(dimethylamino)-1-methylethyl]-1-[2-(4-fluorophenyl)ethyl]-2-methyl-1H-pyrrole-3-carboxamide.

In the same manner as the methods of the above-mentioned Examples 1 to 8, the Example compounds 9 to 220 shown in the following Tables 11 to 33 were produced using respectively corresponding starting materials. Structures and physical data of the Example compounds are shown in the following Tables 11 to 33.

In addition, structures of other compounds of the present invention are shown in Tables 34 to 37. These may be easily synthesized by using the above-mentioned production methods, the methods described in the Examples and the methods which are obvious to those skilled in the art, or modified methods thereof.

TABLE 3

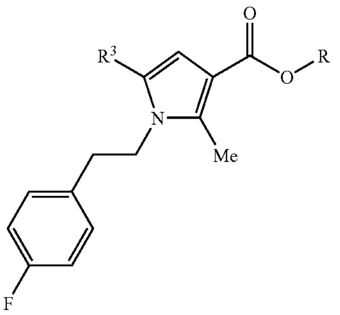

| REx | RSyn | $R^3$ | R | Sal | Dat |
|---|---|---|---|---|---|
| 19 | 1 | iPr | Et | | FAB: 318 |
| 20 | 3 | | H | | FAB: 290 |
| 21 | 3 | $F_3C$— | H | | FAB: 316 |
| 22 | 1 | cPr | Et | | FAB: 316 |
| 23 | 2 | | H | | FAB: 288 |
| 24 | 1 | cBu | Et | | FAB: 330 |
| 25 | 3 | | H | | FAB: 302 |
| 26 | 1 | cPen | Et | | FAB: 344 |
| 27 | 3 | | H | | FAB: 316 |
| 28 | 1 | cHex | Et | | FAB: 358 |
| 2 | 2 | | H | | FAB: 330 |

TABLE 3-continued

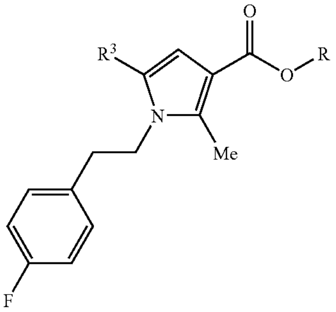

| REx | RSyn | $R^3$ | R | Sal | Dat |
|---|---|---|---|---|---|
| 29 | 1 | 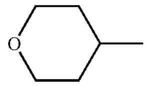 | Et | | FAB: 360 |
| 30 | 3 | | H | | FAB: 332 |
| 31 | 1 | 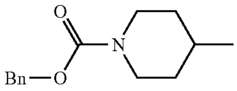 | tBu | | FAB ($M^+$): 520 |
| 32 | 5 | | H | | FN: 463 |
| 4 | 4 | 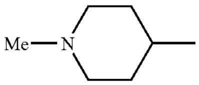 | tBu | | FAB: 401 |
| 5 | 5 | | H | | FAB: 345 |
| 33 | 1 | 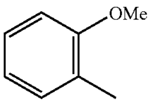 | Et | | FAB: 382 |
| 34 | 3 | | H | | FAB: 354 |
| 35 | 1 | 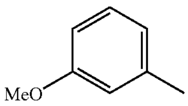 | Et | | FAB: 382 |
| 36 | 3 | | H | | FAB: 354 |
| 37 | 1 | 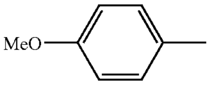 | Et | | FAB: 382 |
| 38 | 3 | | H | | FAB: 354 |
| 39 | 1 | 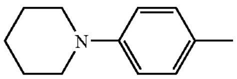 | Et | | ESI: 435 |
| 40 | 3 | | H | | FAB: 407 |
| 41 | 1 | iBu | Et | | FAB: 332 |
| 42 | 2 | | H | | FAB: 304 |

TABLE 4

| | | | | | |
|---|---|---|---|---|---|
| 43 | 1 | 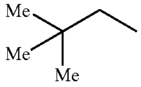 | Et | | FAB: 346 |
| 44 | 3 | | H | | FAB: 318 |
| 45 | 1 | cHex-$CH_2$— | Et | | FAB: 372 |
| 46 | 2 | | H | | FAB: 344 |
| 47 | 1 | 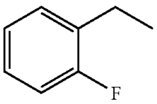 | Et | | FAB: 384 |
| 48 | 3 | | H | | FAB: 356 |

TABLE 4-continued

| | | | | | |
|---|---|---|---|---|---|
| 49 | 1 | 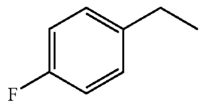 | Et | | FAB: 384 |
| 50 | 3 | | H | | FAB: 356 |
| 51 | 1 | nPr | Et | | FAB: 318 |
| 52 | 2 | | H | | FAB: 290 |
| 53 | 1 | Ph—$(CH_2)_2$— | Et | | FAB: 380 |
| 54 | 2 | | H | | FAB: 352 |
| 55 | 1 | nBu | Et | | FAB: 332 |
| 56 | 2 | | H | | FAB: 304 |
| 57 | 1 | Br—$(CH_2)_3$— | Et | | FAB($M^+$): 396 |
| 58 | 3 | EtO—$(CH_2)_3$— | H | | ESI: 334 |
| 59 | 1 | 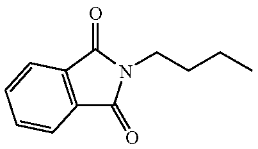 | Bn | | FAB($M^+$): 524 |
| 7 | 7 | $H_2N$—$(CH_2)_3$— | Bn | | FAB: 395 |
| 8 | 8 | $Me_2N$—$(CH_2)_3$— | Bn | | FAB: 423 |
| 9 | 9 | | H | HCl | FAB: 333 |
| 1 | 1 | tBu | Et | | FAB: 332 |
| 3 | 3 | | H | | FAB: 304 |
| 60 | 1, 3 | 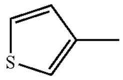 | H | | FAB: 330 |
| 17 | 17 | MeC(O)— | Et | | FAB: 318 |
| 61 | 14 | | H | | FAB: 290 |
| 62 | 1 | Et | Et | | FAB: 304 |

TABLE 5

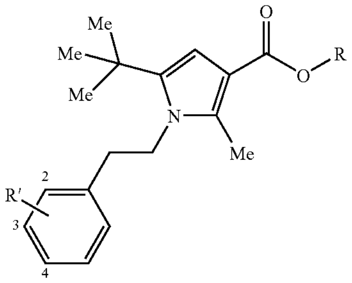

| REx | RSyn | R' | R | Dat |
|---|---|---|---|---|
| 63 | 1 | 4-Cl | Et | FAB: 348 |
| 64 | 3 | | H | FAB: 320 |
| 65 | 1 | 2-OMe | Et | FAB: 344 |
| 66 | 3 | | H | ESI: 316 |
| 67 | 1 | 3-OMe | Et | FAB: 344 |
| 68 | 3 | | H | ESI: 316 |
| 69 | 1 | 4-OMe | Et | FAB: 344 |
| 70 | 3 | | H | ESI: 316 |
| 71 | 1 | null | Et | FAB: 314 |
| 14 | 14 | | H | FAB: 286 |

TABLE 6

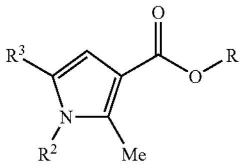

| REx | RSyn | $R^3$ | $R^2$ | R | Dat |
|---|---|---|---|---|---|
| 72 | 1 | tBu | 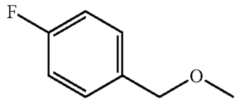 | Et | FAB: 334 |
| 73 | 3 | | | H | FAB: 306 |
| 10 | 10 | Ph | H | Bn | FAB: 292 |
| 11 | 11 | Ph | $BnOCH_2$— | Bn | FAB: 412 |
| 74 | 3 | | | H | FAB: 322 |
| 75 | 11 | Ph | 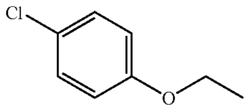 | Bn | FAB: 432 |
| 76 | 3 | | | H | FAB: 342 |

TABLE 7

| REx | RSyn | Str | Dat |
|---|---|---|---|
| 6 | 6 | 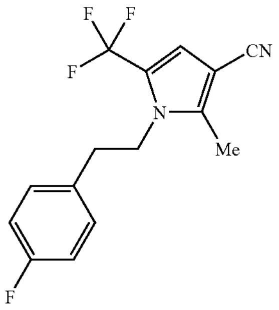 | FAB: 297 |

TABLE 8

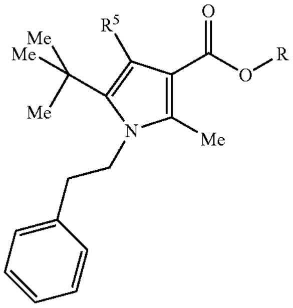

| REx | RSyn | $R^5$ | R | Dat |
|---|---|---|---|---|
| 12 | 12 | HC(O)— | Et | FAB: 360 |
| 13 | 13 | Me | Et | FAB: 328 |
| 77 | 3 | | H | FAB: 300 |

TABLE 9

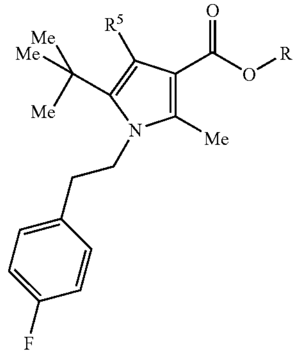

| REx | RSyn | $R^5$ | R | Dat |
|---|---|---|---|---|
| 78 | 12 | HC(O)— | Et | FAB: 360 |
| 79 | 14 | | H | FAB: 332 |
| 80 | 13 | Me | Et | FAB: 346 |
| 81 | 14 | | H | FAB: 318 |
| 15 | 15 | $HOCH_2$— | Et | $FAB(M^+)$: 361 |
| 16 | 16 | $EtOCH_2$— | Et | $ESI(M^+ + Na)$: 412 |
| 82 | 14 | | H | FN: 360 |

TABLE 10

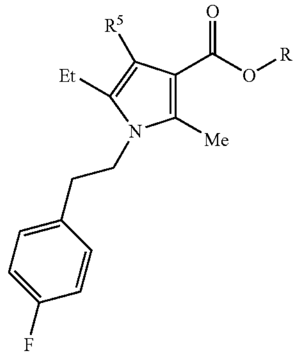

| REx | RSyn | $R^5$ | R | Dat |
|---|---|---|---|---|
| 83 | 17 | MeC(O)— | Et | FAB: 346 |
| 84 | 14 | | H | FAB: 318 |
| 85 | 12 | HC(O)— | Et | FAB: 332 |
| 18 | 18 | MeO—$(CH_2)_2$— | Et | FAB: 362 |
| 86 | 14 | | H | FAB: 334 |

TABLE 11

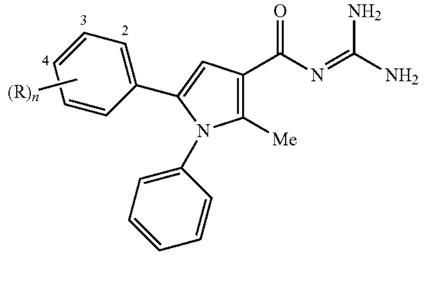

| Ex | Syn | $(R)_n$— | Dat |
|---|---|---|---|
| 9 | 7 | null | ESI: 319 |
| 10 | 7 | 3-F | ESI: 337 |
| 11 | 7 | 3-OMe | ESI: 349 |

TABLE 11-continued

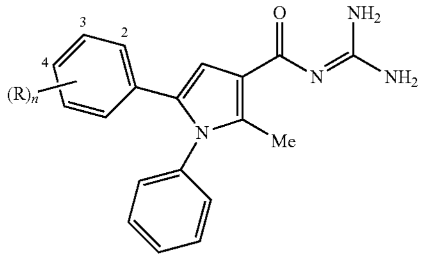

| Ex | Syn | $(R)_n$— | Dat |
|---|---|---|---|
| 12 | 7 | 4-F | ESI: 337 |
| 13 | 7 | 2-Cl | ESI: 353 |
| 14 | 7 | 4-OMe | ESI: 349 |
| 15 | 7 | 2,4-diOMe | ESI: 379 |
| 16 | 7 | 4-Me | ESI: 333 |
| 17 | 7 | 4-Cl | ESI: 353 |
| 18 | 7 | 2-$CF_3$ | ESI: 387 |
| 19 | 7 | 2,4-diMe | ESI: 347 |
| 20 | 7 | 3,4-diCl | ESI: 387 |
| 21 | 7 | 3-Me-4-Cl | ESI: 367 |
| 22 | 7 | 2-F | ESI: 337 |
| 23 | 7 | 3,4-diF | ESI: 355 |
| 24 | 7 | 3-Cl | ESI: 353 |

TABLE 12

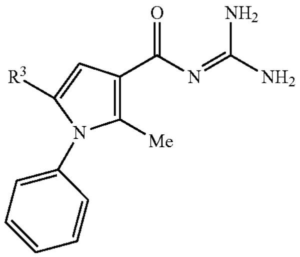

| Ex | Syn | $R^3$ | Dat |
|---|---|---|---|
| 25 | 7 | tBu | ESI: 337 |
| 26 | 7 | 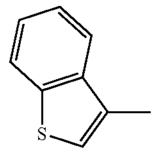 | ESI: 375 |
| 27 | 7 | 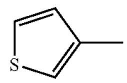 | ESI: 325 |
| 28 | 7 | 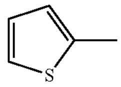 | ESI: 325 |
| 29 | 7 | 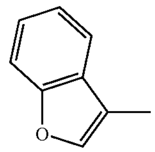 | ESI: 359 |

TABLE 13

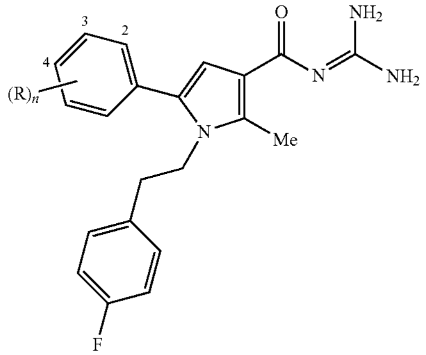

| Ex | Syn | $(R)_n$— | Sal | Dat |
|---|---|---|---|---|
| 30 | 7 | null | | ESI: 365 |
| 5 | 5 | 2-OH | HCl | FAB: 381 |
| 31 | 5 | 3-OH | HCl | FAB: 381 |
| 32 | 5 | 4-OH | HCl | FAB: 381 |
| 33 | 7 | 2,5-diOMe | | ESI: 425 |
| 34 | 7 | 3-OMe | | ESI: 395 |
| 35 | 7 | $2\text{-}NO_2$ | | ESI: 410 |
| 36 | 7 | $3\text{-}NO_2$ | | ESI: 410 |
| 37 | 7 | 4-F | | ESI: 383 |
| 38 | 7 | $3\text{-}CF_3$ | | ESI: 433 |
| 39 | 7 | 3,4-diF | | ESI: 401 |
| 40 | 7 | 3-Cl | | ESI: 399 |
| 41 | 7 | 2-Cl | | ESI: 399 |
| 7 | 7 | 3-F | | ESI: 383 |
| 42 | 7 | $2\text{-}CF_3$ | | ESI: 433 |
| 43 | 7 | 2-OMe-5-F | | ESI: 413 |
| 44 | 7 | 2,6-diF | | ESI: 401 |
| 45 | 7 | 3,5-diF | | ESI: 401 |
| 46 | 7 | 2,4-diF | | ESI: 401 |
| 47 | 7 | 2-F | | ESI: 383 |

TABLE 14

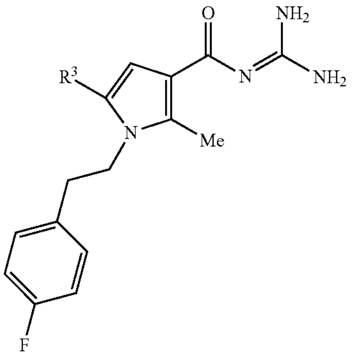

| Ex | Syn | $R^3$ | Sal | Dat |
|---|---|---|---|---|
| 48 | 1 | iPr | HCl | FAB: 331 |
| 49 | 1 | $F_3C$— | HCl | FAB: 357 |
| 50 | 1 | cPr | Oxa | FAB: 329 |
| 51 | 1 | cBu | HCl | FAB: 343 |
| 52 | 1 | cPen | HCl | FAB: 357 NMR: 1.40-1.98 (8H, m), 2.39 (3H, s), 2.81-2.93 (3H, m), 4.08 (2H, t, J = 7.2 Hz), 6.90 (1H, s), 7.07-7.19 (4H, m), 8.24 (2H, br s), 8.79 (2H, br s), 11.01 (1H, s) |

TABLE 14-continued

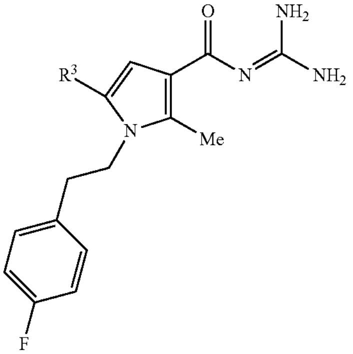

| Ex | Syn | $R^3$ | Sal | Dat |
|---|---|---|---|---|
| 1 | 1 | cHex | HCl | FAB: 371 |
| 53 | 1 | 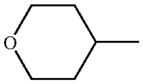 | HCl | FAB: 373 |
| 4 | 4 | 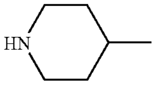 | 2HCl | FAB: 372 |
| 54 | 1 | 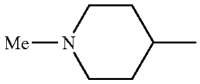 | 2HCl | FAB: 386 |
| 55 | 1 | 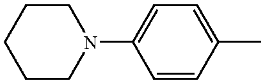 | 2HCl | ESI: 448 |
| 56 | 1 | iBu | HCl | FAB: 345 |
| 57 | 1 | tBu—$CH_2$— | HCl | FAB: 359 |
| 58 | 1 | cHex—$CH_2$— | HCl | FAB: 385 |
| 59 | 1 | 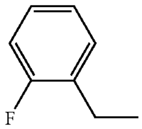 | HCl | FAB: 397 |
| 60 | 1 | 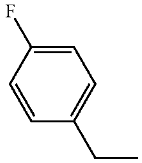 | HCl | FAB: 397 |
| 61 | 1 | nPr | HCl | FAB: 331 |

TABLE 15
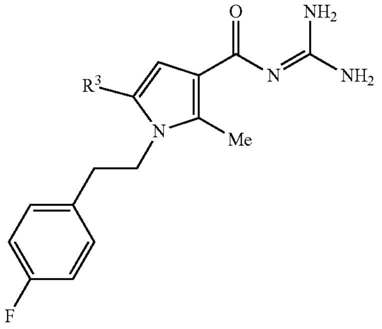
| | | | | |
|---|---|---|---|---|
| 62 | 1 | Ph—$(CH_2)_2$— | HCl | FAB: 393 |
| 63 | 1 | nBu | HCl | FAB: 345 |
| 64 | 1 | EtO—$(CH_2)_3$— | HCl | FAB: 375 |
| 65 | 1 | $Me_2N$—$(CH_2)_3$— | 2HCl | FAB: 374 |
| 66 | 7 | tBu | | ESI: 345 |
| 67 | 7 | 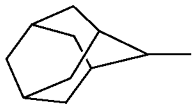 | | ESI: 423 |
| 68 | 7 | 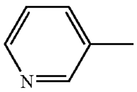 | | ESI: 366 |
| 69 | 7 | 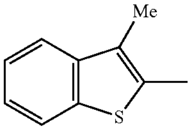 | | ESI: 435 |
| 70 | 7 | 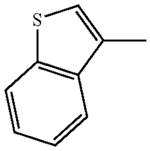 | | ESI: 421 |
| 71 | 7 | 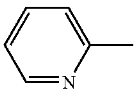 | | ESI: 366 |
| 72 | 7 | 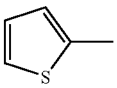 | | ESI: 371 |
| 73 | 7 | 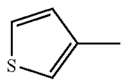 | | ESI: 371 |
| 74 | 7 | 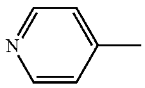 | | ESI: 366 |
| 75 | 7 | 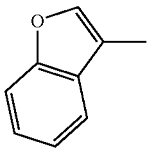 | | ESI: 405 |
TABLE 15-continued
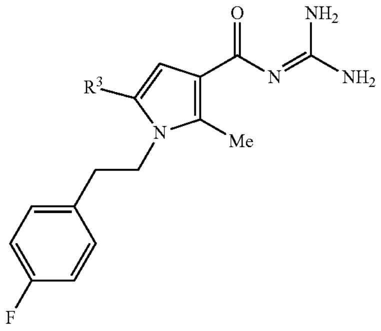
| | | | | |
|---|---|---|---|---|
| 76 | 7 | 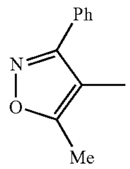 | | ESI: 446 |
| 77 | 7 | 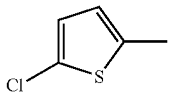 | | ESI: 405 |
| 78 | 7 | Et | | ESI: 317 |
| 79 | 7 | Me | | ESI: 303 |
TABLE 16
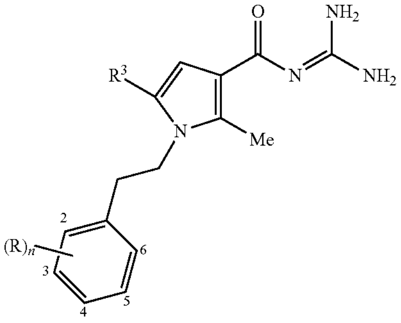
| Ex | Syn | $(R)_n$— | $R^3$ | Sal | Dat |
|---|---|---|---|---|---|
| 80 | 1 | 4-Cl | tBu | HCl | FAB: 361 |
| 3 | 3 | 2-OH | tBu | HCl | FAB: 343 |
| 81 | 3 | 3-OH | tBu | Oxa | FAB: 343 |
| 82 | 3 | 4-OH | tBu | HCl | FAB: 343 |
| 83 | 7 | 2-F | Ph | | ESI: 365 |
| 84 | 7 | 3-F | Ph | | ESI: 365 |
| 85 | 7 | 3-Cl | Ph | | ESI: 381 |
| 86 | 7 | 3-Me | Ph | | ESI: 361 |
| 87 | 7 | 4-Cl | Ph | | ESI: 381 |
| 88 | 7 | 4-Me | Ph | | ESI: 361 |
| 89 | 7 | 2-Cl | Ph | | ESI: 381 |
| 90 | 7 | 2,5-diOMe | Ph | | ESI: 407 |

TABLE 17
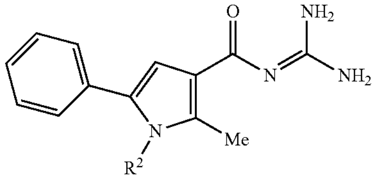
| Ex | Syn | $R^2$ | Sal | Dat |
|---|---|---|---|---|
| 91 | 1 | $BnOCH_2$— | HCl | FAB: 363 |
| 92 | 1 | 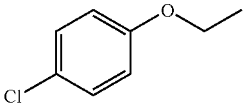 | Oxa | FAB: 383 |
| 93 | 7 | 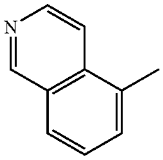 | | ESI: 370 |
| 94 | 7 | 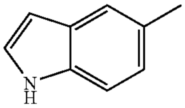 | | ESI: 358 |
| 95 | 7 | 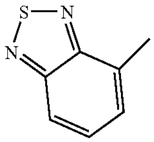 | | ESI: 377 |
| 96 | 7 | cPr—$CH_2$— | | ESI: 297 |
| 97 | 7 | 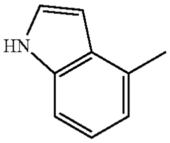 | | ESI: 358 |
| 98 | 7 | 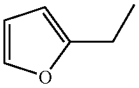 | | ESI: 323 |
| 99 | 7 | Ph—$(CH_2)_2$— | | ESI: 347 |
| 100 | 7 | 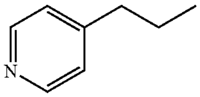 | | ESI: 348 |
| 101 | 7 | 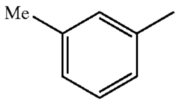 | | ESI: 333 |
| 102 | 7 | 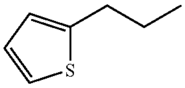 | | ESI: 353 |
| 103 | 7 | nPr | | ESI: 285 |
| 104 | 7 | cPen | | ESI: 311 |
TABLE 18
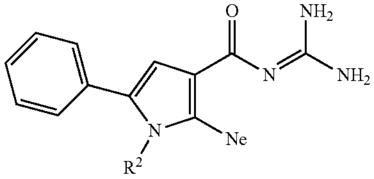
| | | | |
|---|---|---|---|
| 105 | 7 | 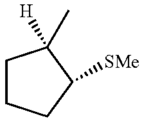 | ESI: 357 |
| 106 | 7 | cHep | ESI: 339 |
| 107 | 7 | cOct | ESI: 353 |
| 108 | 7 | NC—$CH_2$— | ESI: 281 |
| 109 | 7 | MeS—$(CH_2)_3$— | ESI: 331 |
| 110 | 7 | 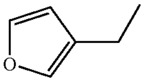 | ESI: 323 |
| 111 | 7 | 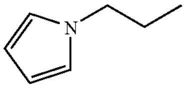 | ESI: 336 |
| 112 | 7 | tBu—$(CH_2)_2$— | ESI: 327 |
| 113 | 7 | 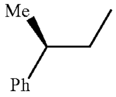 | ESI: 361 |
| 114 | 7 | $PhC(O)CH_2$— | ESI: 361 |
| 115 | 7 | cBu | ESI: 297 |
| 116 | 7 | $HOCH_2CH(Et)$— | ESI: 315 |
| 117 | 7 | BnO— | ESI: 349 |
| 118 | 7 | 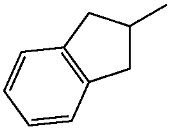 | ESI: 359 |
| 119 | 7 | 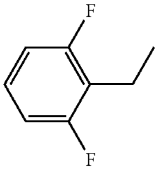 | ESI: 369 |
| 120 | 7 | 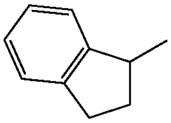 | ESI: 359 |
| 121 | 7 | $PhCH(OH)CH_2$— | ESI: 363 |

TABLE 18-continued
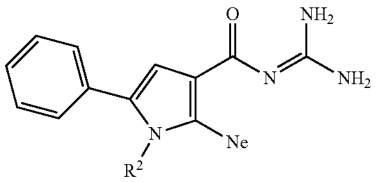
| | | | |
|---|---|---|---|
| 122 | 7 | 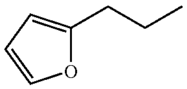 | ESI: 337 |
| 123 | 7 | 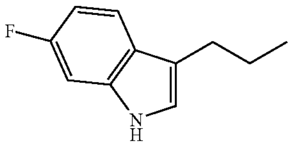 | ESI: 404 |
TABLE 19
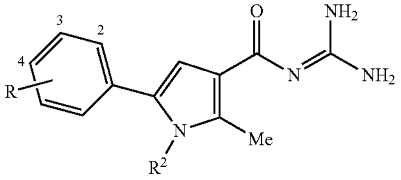
| Ex | Syn | $R^2$ | R | Dat |
|---|---|---|---|---|
| 124 | 7 | cBu | 2-F | ESI: 315 |
| 125 | 7 | | 3-F | ESI: 315 |
| 126 | 7 | cPen | 2-F | ESI: 329 |
| 127 | 7 | | 3-F | ESI: 329 |
| 128 | 7 | cHex | 2-F | ESI: 343 |
| 129 | 7 | | 3-F | ESI: 343 |
| 130 | 7 | 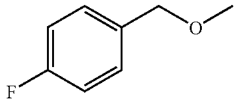 | 2-F | ESI: 385 |
| 131 | 7 | | 3-F | ESI: 385 |
TABLE 20
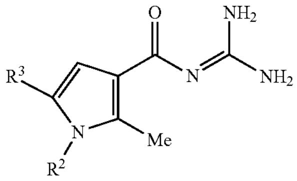
| Ex | Syn | $R^2$ | $R^3$ | Sal | Dat |
|---|---|---|---|---|---|
| 132 | 1 | H | tBu | HCl | FAB: 243 |
| 133 | 7 | cBu | 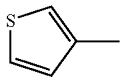 | | ESI: 303 |
| 134 | 7 | cPen | 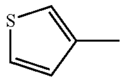 | | ESI: 317 |
| 135 | 7 | | 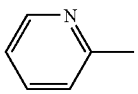 | | ESI: 312 |
| 136 | 1 | 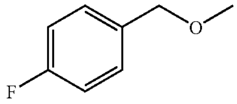 | tBu | HCl | FAB: 347 |
| 137 | 7 | | 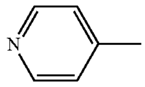 | | ESI: 368 |
| 138 | 7 | | 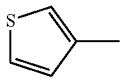 | | ESI: 373 |

TABLE 21
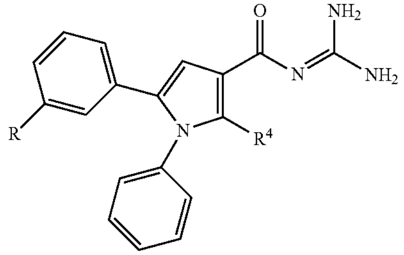
| Ex | Syn | R | $R^4$ | Dat |
|---|---|---|---|---|
| 139 | 7 | H | 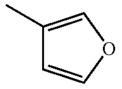 | ESI: 371 |
| 140 | 7 | H | Et | ESI: 313 |
| 141 | 7 | F | Et | ESI: 351 |
TABLE 22
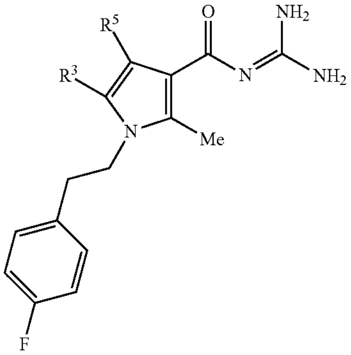
| Ex | Syn | $R^3$ | $R^5$ | Sal | Dat |
|---|---|---|---|---|---|
| 142 | 1 | tBu | Me | 0.5Oxa | FAB: 359 |
| 143 | 1 | Et | MeO—$(CH_2)_2$— | Oxa | FAB: 375 |
TABLE 23
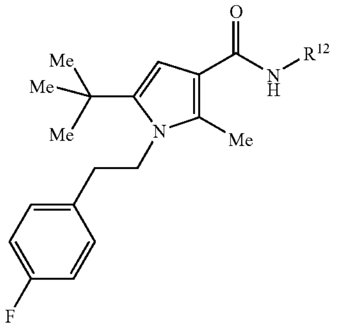
| Ex | Syn | $R^{12}$ | Sal | Dat |
|---|---|---|---|---|
| 2 | 2 | —$(CH_2)_2$—$NMe_2$ | HCl | FAB: 374 NMR: 1.34 (9H, s), 2.57 (3H, s), 2.80 (3H, s), 2.81 (3H, s), 2.85-2.89 (2H, m), 3.16-3.20 (2H, m), 3.50-3.54 (2H, m), 4.11-4.15 |
TABLE 23-continued
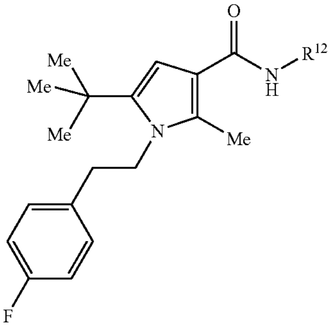
| Ex | Syn | $R^{12}$ | Sal | Dat |
|---|---|---|---|---|
| | | | | (2H, m), 6.36 (1H, s), 7.15-7.21 (2H, m), 7.30-7.35 (2H, m), 7.93 (1H, t, J = 5.6Hz), 10.22 (1H, brs) |
| 144 | 2 | —$(CH_2)_2$—NHMe | Oxa | FAB: 360 |
| 145 | 2 | —$CH_2C(Me)_2NMe_2$ | Oxa | FAB: 402 NMR: 1.28 (6H, s), 1.35 (9H, s), 2.57 (3H, s), 2.77 (6H, s), 2.85-2.90 (2H, m), 3.48 (2H, d, J = 6.4Hz), 4.11-4.16 (2H, m), 6.37 (1H, s), 7.16-7.20 (2H, m), 7.32-7.35 (2H, m), 7.77 (1H, t, J = 6.4Hz) |
| 146 | 2 | 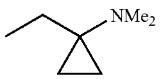 | Oxa | FAB: 400 |
| 147 | 2 | 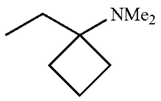 | Oxa | FAB: 414 |
| 148 | 2 | 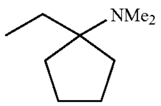 | HCl | FAB: 428 |
| 149 | 2 | 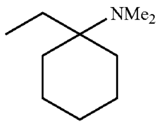 | Oxa | FAB: 442 |
| 150 | 2 | 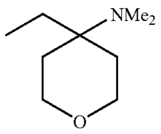 | Oxa | FAB: 444 |

TABLE 24
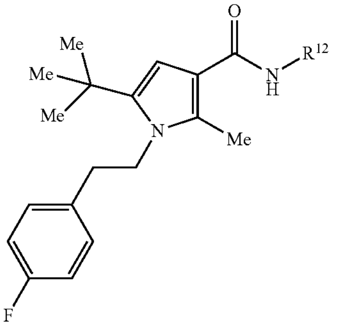
| | | | | |
|---|---|---|---|---|
| 151 | 2 | 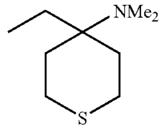 | Oxa | FAB: 460 |
| 6 | 6 | 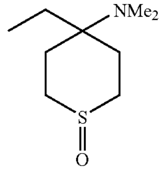 | Oxa | FAB: 476 |
| 152 | 2 | 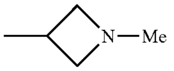 | Oxa | FAB: 372 |
| 153 | 2 | 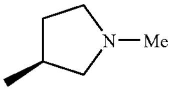 | Oxa | FAB: 386<br>NMR: 1.34 (9H, s), 1.96-2.05 (1H, m), 2.27-2.36 (1H, m), 2.55 (3H, s),<br>2.81 (3H, s), 2.85-2.89 (2H, m), 3.19-3.22 (2H, m), 3.43-3.45 (2H, m), 4.10.4.14 (2H, m), 4.47-4.56 (1H, m), 6.30 (1H, s), 7.15-7.20 (2H, m), 7.30-7.34 (2H, m), 7.83 (1H, d, J = 6.8Hz) |
| 154 | 2 | 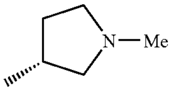 | Oxa | FAB: 386<br>NMR: 1.34 (9H,s), 1.96-2.04 (1H, m), 2.26-2.35 (1H, m), 2.55 (3H, s),<br>2.81 (3H, s), 2.84-2.89 (2H, m), 3.18-3.21 (2H, m), 3.43-3.44 (2H, m), 4.10-4.14 (2H, m), 4.45-4.53 (1H, m), 6.29 (1H, s), 7.15-7.20 (2H, m), 7.30-7.34 (2H, m), 7.81 (1H, d, J = 6.6Hz) |
| 155 | 2 | 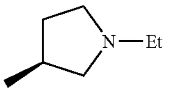 | Oxa | FAB: 400 |
| 156 | 2 | 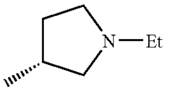 | Oxa | FAB: 400 |
| 157 | 2 | 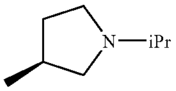 | Oxa | FAB: 414 |
| 158 | 2 | 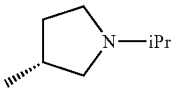 | Oxa | FAB: 414 |
TABLE 24-continued
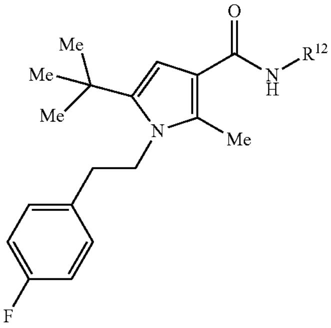
| | | | | |
|---|---|---|---|---|
| 159 | 2 | 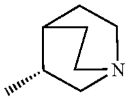 | Oxa | FAB: 412 |
TABLE 25
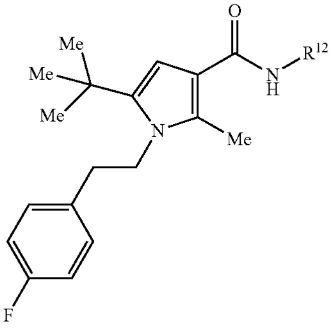
| | | | | |
|---|---|---|---|---|
| 160 | 2 | 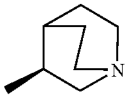 | Oxa | FAB: 412 |
| 161 | 2 | 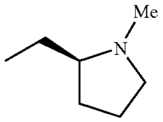 | Oxa | FAB: 400<br>NMR: 1.34 ( 9H, s), 1.73-1.89 (2H, m), 1.91-2.00 (1H, m), 2.05-2.15 (1H, m), 2.56 (3H, s), 2.85-2.90 (5H, m), 2.99-3.06 (1H, m), 3.40-3.47 (1H, m), 3.51-3.53 (3H, m), 4.11-4.15 (2H, m), 6.30 (1H, s), 7.15-7.20 (2H, m), 7.31-7.34 (2H, m), 8.00-8.03 (1H, m) |
| 162 | 2 | 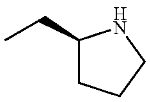 | Oxa | FAB: 386 |
| 163 | 2 | 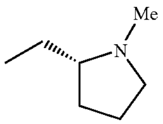 | Oxa | FAB: 400<br>NMR: 1.34 (9H, s), 1.76-1.87 (2H, m), 1.92-1.99 (1H, m), 2.07-2.11 (1H, m), 2.56 (3H, s), 2.85-2.90 (5H, m), 3.00-3.03 (1H, m), 3.42-3.44 (1H, m), 3.51-3.56 (3H, m), 4.11-4.15 (2H, m), 6.30 (1H, s), 7.15-7.20 (2H, m), 7.31-7.34 (2H, m), 8.00-8.03 (1H, m) |
| 164 | 8 | $-(CH_2)_3-NMe_2$ | | ESI: 388 |
| 8 | 8 | $-CH(Me)CH_2NMe_2$ | | ESI: 388 |
| 165 | 8 | $-(CH_2)_2-NEt_2$ | | ESI: 402 |

TABLE 25-continued
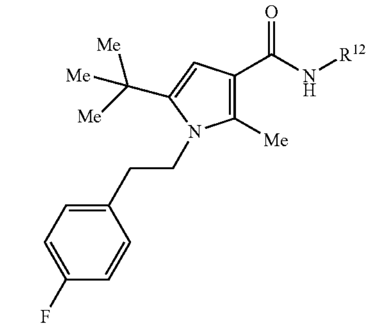
| | | | | |
|---|---|---|---|---|
| 166 | 2 | 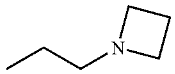 | HCl | ESI: 386 |
| 167 | 8 | 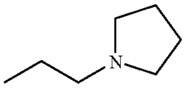 | | ESI: 400 |
| 168 | 8 | 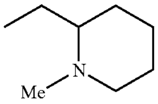 | | ESI: 414 |
| 169 | 8 | 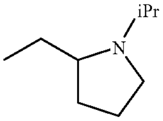 | | ESI: 428 |
| 170 | 8 | —$CH_2CH(Ph)NMe_2$ | | ESI: 450 |
TABLE 26
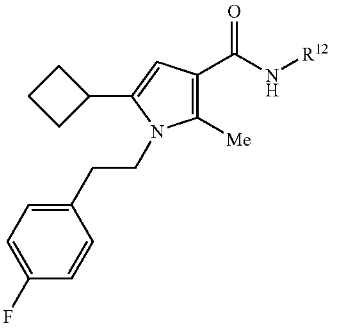
| Ex | Syn | $R^{12}$ | Dat |
|---|---|---|---|
| 171 | 8 | —$(CH_2)_2$—$NMe_2$ | ESI: 372 |
| 172 | 8 | —$CH(Me)CH_2NMe_2$ | ESI: 386 |
| 173 | 8 | —$(CH_2)_2$—$NEt_2$ | ESI: 400 |
| 174 | 8 | 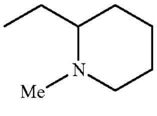 | ESI: 412 |
| 175 | 8 | 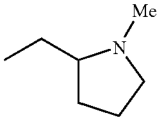 | ESI: 412 |
TABLE 26-continued
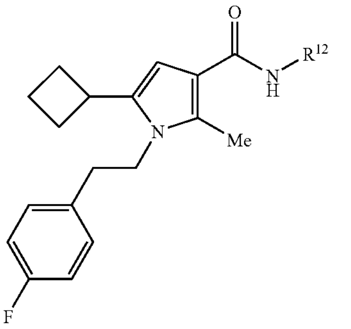
| Ex | Syn | $R^{12}$ | Dat |
|---|---|---|---|
| 176 | 8 | 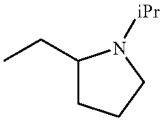 | ESI: 426 |
| 177 | 8 | —$CH_2CH(Ph)NMe_2$ | ESI: 448 |
TABLE 27
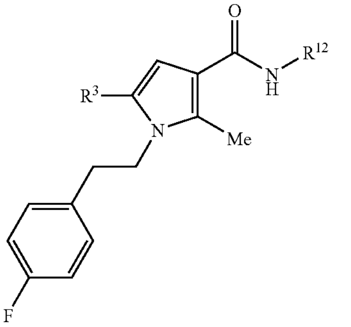
| Ex | Syn | $R^3$ | $R^{12}$ | Dat |
|---|---|---|---|---|
| 178 | 8 | Ph | 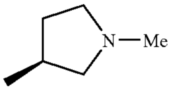 | ESI: 406 |
| 179 | 8 | 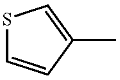 | | ESI: 412 |
| 180 | 8 | 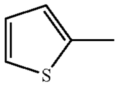 | | ESI: 412 |
| 181 | 8 | 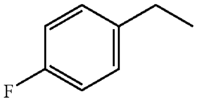 | | ESI: 438 |
| 182 | 8 | 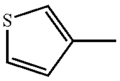 | 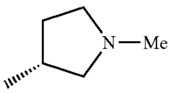 | ESI: 412 |

TABLE 27-continued
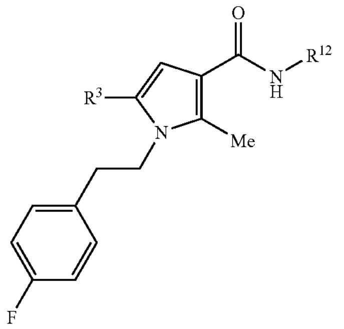
| Ex | Syn | $R^3$ | $R^{12}$ | Dat |
|---|---|---|---|---|
| 183 | 8 | 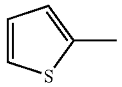 | | ESI: 412 |
| 184 | 8 | 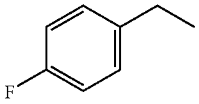 | | ESI: 438 |
TABLE 28
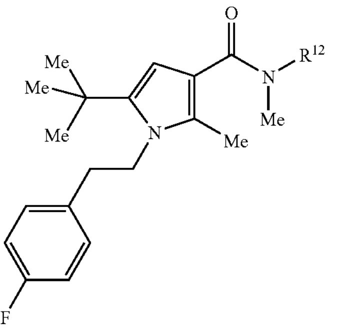
| Ex | Syn | $R^{12}$ | Dat |
|---|---|---|---|
| 185 | 8 | 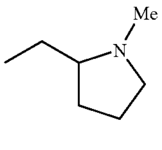 | ESI: 414 |
| 186 | 8 | 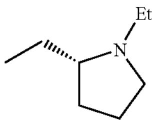 | ESI: 414 |
TABLE 29
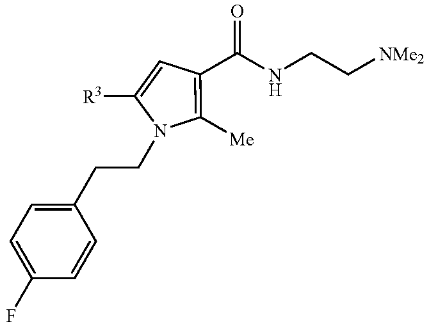
| Ex | Syn | $R^3$ | Sal | Dat |
|---|---|---|---|---|
| 187 | 2 | 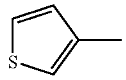 | HCl | FAB: 400 |
| 188 | 8 | 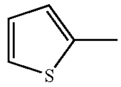 | | ESI: 400 |
| 189 | 8 | 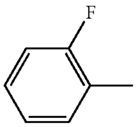 | | ESI: 412 |
| 190 | 8 | 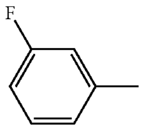 | | ESI: 412 |
| 191 | 8 | 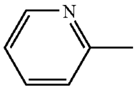 | | ESI: 395 |
| 192 | 8 | 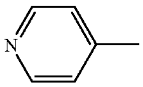 | | ESI: 395 |
| 193 | 8 | iBu | | ESI: 374 |
| 194 | 8 | cHex | | ESI: 400 |
| 195 | 8 | 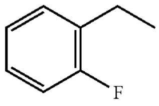 | | ESI: 426 |
| 196 | 8 | 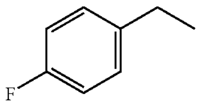 | | ESI: 426 |
| 197 | 8 | Ph—$(CH_2)_2$— | | ESI: 422 |
| 198 | 8 | Ph | | ESI: 394 |
| 199 | 8 | 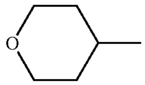 | | ESI: 402 |
| 200 | 2 | MeC(O)— | Oxa | FAB: 360 |

TABLE 30
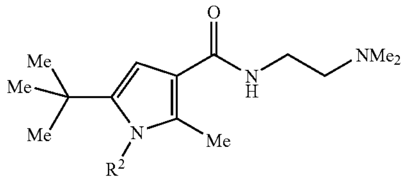
| Ex | Syn | $R^2$ | Sal | Dat |
|---|---|---|---|---|
| 201 | 2 | Ph—$(CH_2)_2$— | Oxa | FAB: 356 |
| 202 | 8 | 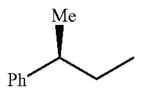 | | ESI: 370 |
| 203 | 8 | 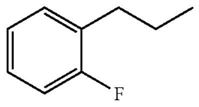 | | ESI: 374 |
| 204 | 8 | 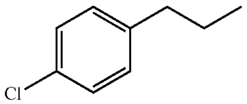 | | ESI: 390 |
| 205 | 8 | 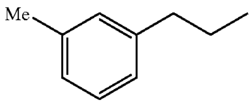 | | ESI: 370 |
| 206 | 8 | 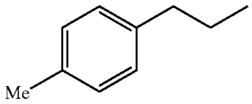 | | ESI: 370 |
| 207 | 8 | 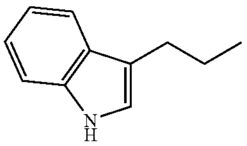 | | ESI: 395 |
| 208 | 8 | 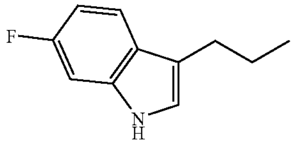 | | ESI: 413 |
| 209 | 8 | 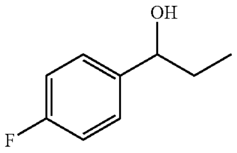 | | ESI: 390 |
| 210 | 8 | BnO— | | ESI: 358 |
| 211 | 8 | 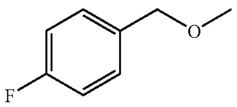 | | ESI: 376 |
TABLE 31
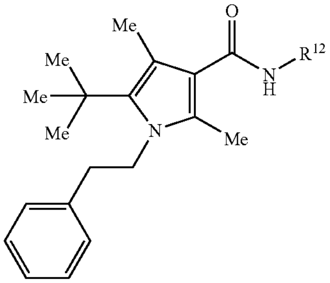
| Ex | Syn | $R^{12}$ | Sal | Dat |
|---|---|---|---|---|
| 212 | 2 | —$(CH_2)_2$—$NMe_2$ | Oxa | FAB: 370 |
| 213 | 2 | 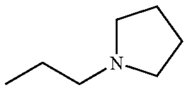 | Oxa | FAB: 396 |
TABLE 32
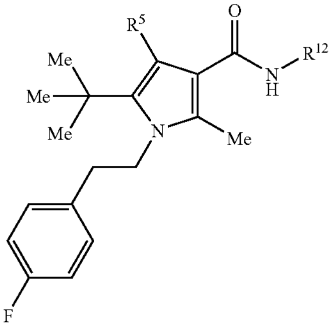
| Ex | Syn | $R^5$ | $R^{12}$ | Sal | Dat |
|---|---|---|---|---|---|
| 214 | 2 | HC(O)— | —$(CH_2)_2$—$NMe_2$ | Fum | FAB: 402 |
| 215 | 2 | Me | —$(CH_2)_2$—$NMe_2$ | Fum | FAB: 388 |
| 216 | 2 | EtO—$CH_2$— | —$(CH_2)_2$—$NMe_2$ | | FAB: 432 |
| 217 | 2 | Me | 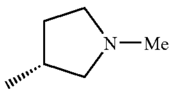 | Oxa | FAB: 400 |
| 218 | 2 | Me | 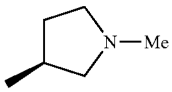 | Oxa | FAB: 400 |

TABLE 33

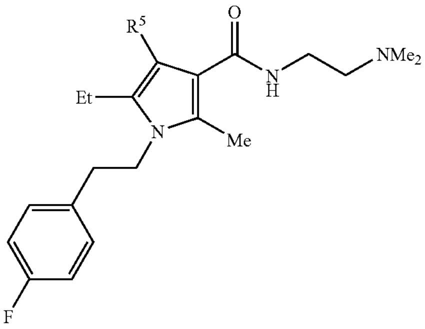

| Ex | Syn | $R^5$ | Sal | Dat |
|---|---|---|---|---|
| 219 | 2 | MeC(O)— | Oxa | FAB: 388 |
| 220 | 2 | $MeO—(CH_2)_2—$ | Oxa | FAB: 404 |

TABLE 34

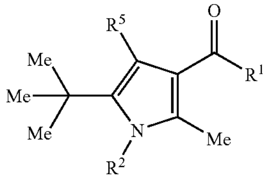

| No. | $R^5$ | $R^2$ | $R^1$ |
|---|---|---|---|
| 1<br>2<br>3 | Me<br>cHex<br>Ph | Ph | 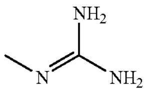 |
| 4<br>5<br>6 | Me<br>cHex<br>Ph | 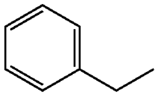 | |
| 7<br>8<br>9 | Me<br>cHex<br>Ph | 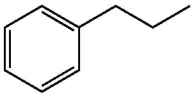 | |
| 10<br>11 | cHex<br>Ph | 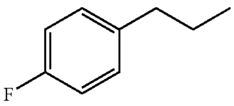 | |
| 12<br>13 | cHex<br>Ph | Ph | 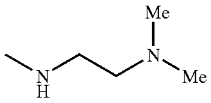 |
| 14<br>15<br>16 | Me<br>cHex<br>Ph | 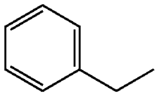 | |
| 17<br>18<br>19 | Me<br>cHex<br>Ph | 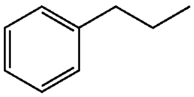 | |

TABLE 34-continued

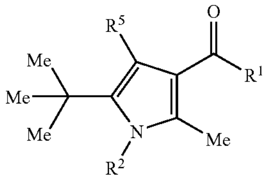

| No. | $R^5$ | $R^2$ | $R^1$ |
|---|---|---|---|
| 20<br>21 | cHex<br>Ph | 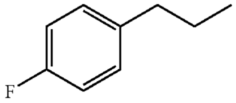 | |
| 22<br>23 | cHex<br>Ph | Ph | 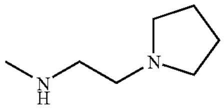 |
| 24<br>25<br>26 | Me<br>cHex<br>Ph | 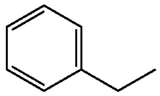 | |
| 27<br>28<br>29 | Me<br>cHex<br>Ph | 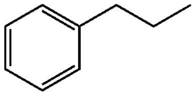 | |
| 30<br>31<br>32 | Me<br>cHex<br>Ph | 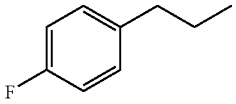 | |

TABLE 35

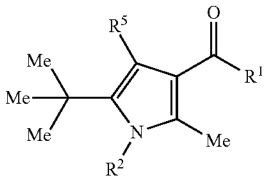

| No. | $R^5$ | $R^2$ | $R^1$ |
|---|---|---|---|
| 33<br>34<br>35 | Me<br>cHex<br>Ph | Ph | 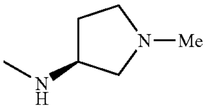 |
| 36<br>37<br>38 | Me<br>cHex<br>Ph | 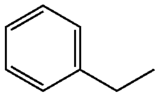 | |
| 39<br>40<br>41 | Me<br>cHex<br>Ph | 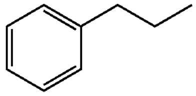 | |
| 42<br>43 | cHex<br>Ph | 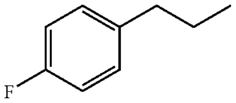 | |

TABLE 35-continued
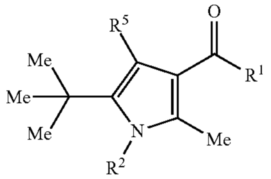
| No. | $R^5$ | $R^2$ | $R^1$ |
|---|---|---|---|
| 44 | Me | Ph | 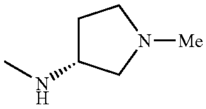 |
| 45 | cHex | | |
| 46 | Ph | | |
| 47 | Me | 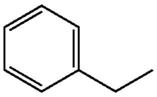 | |
| 48 | cHex | | |
| 49 | Ph | | |
| 50 | Me | 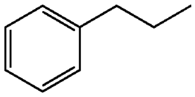 | |
| 51 | cHex | | |
| 52 | Ph | | |
| 53 | cHex | 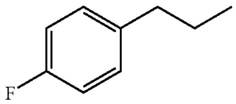 | |
| 54 | Ph | | |
TABLE 36
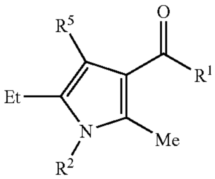
| No. | $R^5$ | $R^2$ | $R^1$ |
|---|---|---|---|
| 55 | Me | Ph | 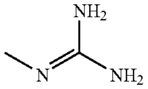 |
| 56 | cHex | | |
| 57 | Ph | | |
| 58 | Me | 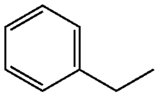 | |
| 59 | cHex | | |
| 60 | Ph | | |
| 61 | Me | 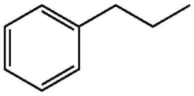 | |
| 62 | cHex | | |
| 63 | Ph | | |
| 64 | Me | 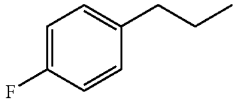 | |
| 65 | cHex | | |
| 66 | Ph | | |
| 67 | Me | Ph | 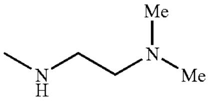 |
| 68 | cHex | | |
| 69 | Ph | | |
| 70 | Me | 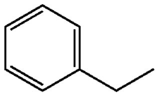 | |
| 71 | cHex | | |
| 72 | Ph | | |
TABLE 36-continued
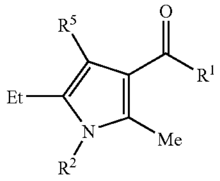
| No. | $R^5$ | $R^2$ | $R^1$ |
|---|---|---|---|
| 73 | Me | 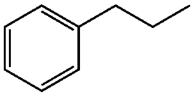 | |
| 74 | cHex | | |
| 75 | Ph | | |
| 76 | Me | 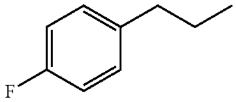 | |
| 77 | cHex | | |
| 78 | Ph | | |
| 79 | Me | Ph | 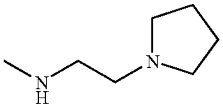 |
| 80 | cHex | | |
| 81 | Ph | | |
| 82 | Me | 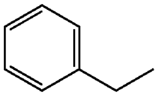 | |
| 83 | cHex | | |
| 84 | Ph | | |
| 85 | Me | 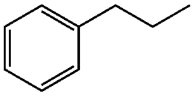 | |
| 86 | cHex | | |
| 87 | Ph | | |
| 88 | Me | 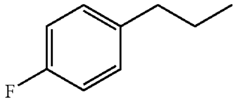 | |
| 89 | cHex | | |
| 90 | Ph | | |
TABLE 37
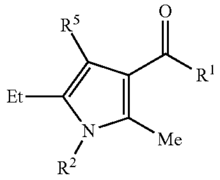
| | | | |
|---|---|---|---|
| 91 | Me | Ph | 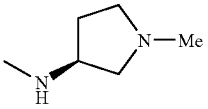 |
| 92 | cHex | | |
| 93 | Ph | | |
| 94 | Me | 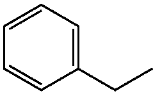 | |
| 95 | cHex | | |
| 96 | Ph | | |
| 97 | Me | 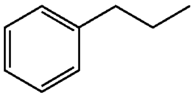 | |
| 98 | cHex | | |
| 99 | Ph | | |

TABLE 37-continued

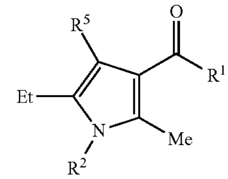

| | | | |
|---|---|---|---|
| 100 | Me | 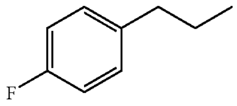 | |
| 101 | cHex | | |
| 102 | Ph | | |
| 103 | Me | Ph | 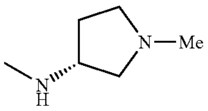 |
| 104 | cHex | | |
| 105 | Ph | | |
| 106 | Me | 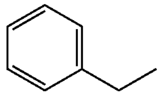 | |
| 107 | cHex | | |
| 108 | Ph | | |
| 109 | Me | 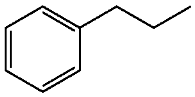 | |
| 110 | cHex | | |
| 111 | Ph | | |
| 112 | Me | 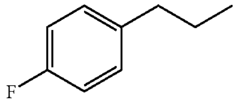 | |
| 113 | cHex | | |
| 114 | Ph | | |

INDUSTRIAL APPLICABILITY

Since the compound of the present invention has excellent antagonistic activity for both of the 5-$HT_{2B}$ and 5-$HT_7$ receptors, it is useful as a pharmaceutical, particularly as a therapeutic agent for IBS.

The invention claimed is:

1. A compound represented by formula (I) or a pharmaceutically acceptable salt thereof (I)

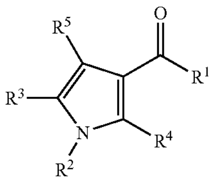

wherein $R^1$ is —N═C($NH_2$)$_2$, —N($R^0$)-(nitrogen-containing saturated heterocyclic group which has a linkage on a carbon atom as the ring atom and may be substituted), —N($R^0$) lower alkylene-N(lower alkyl)$_2$, —N($R^0$)-lower alkylene-(nitrogen-containing saturated heterocyclic group which may be substituted), —N($R^0$)-lower alkylene-(heterocyclic group substituted with —N(lower alkyl)$_2$) or —N($R^0$)-lower alkylene-(cycloalkyl substituted with —N(lower alkyl)$_2$);

$R^0$ is independently —H or lower alkyl;

$R^3$ is lower alkyl;

$R^4$ is lower alkyl;

$R^5$ is —H or lower alkyl; and $R^2$ is —($CH_2$)$_2$)-(phenyl which may be substituted with halogen).

2. The compound described in claim 1, wherein $R^1$ is —N═C($NH_2$)$_2$, —N($R^0$)-(nitrogen-containing saturated heterocyclic group which has a linkage on a carbon atom as the ring atom and may be substituted with lower alkyl), —N($R^0$)-lower alkylene-N(lower alkyl)$_2$ or —N($R^0$)-lower alkylene-(nitrogen-containing saturated heterocyclic group which may be substituted with lower alkyl).

3. A compound, which is selected from the group consisting of:

5-tert-butyl-1-[2-(4-fluorophenyl)ethyl]-2-methyl-N-[(3S)-1-methylpyrrolidin-3-yl]-1H-pyrrole-3-carboxamide, 5-tert-butyl-1-[2-(4-fluorophenyl)ethyl]-2-methyl-N-[(3R)-1-methylpyrrolidin-3-yl]-1H-pyrrole-3-carboxamide, 5-tert-butyl-1-[2-(4-fluorophenyl)ethyl]-2,4-dimethyl-N-[(3S)-1-methylpyrrolidin-3-yl]-1H-pyrrole-3-carboxamide, 5-tert-butyl-1-[2-(4-fluorophenyl)ethyl]-2,4-dimethyl-N-[(3R)-1-methylpyrrolidin-3-yl]-1H-pyrrole-3-carboxamide, 5-tert-butyl-1-[2-(dimethylamino)ethyl]-1-[2-(4-fluorophenyl)ethyl]-2-methyl-1H-pyrrole-3-carboxamide, 5-tert-butyl-1-[2-(4-fluorophenyl)ethyl]-2-methyl-N-{[(2R)-1-methylpyrrolidin-2-yl]methyl}-1H-pyrrole-3-carboxamide, and 5-tert-butyl-1-[2-(4-fluorophenyl)ethyl]-2-methyl-N-{[(2S)-1-methylpyrrolidin-2-yl]methyl}-1H-pyrrole-3-carboxamide, or a pharmaceutically acceptable salt thereof.

4. A pharmaceutical composition which comprises the compound described in claim 1 or a pharmaceutically acceptable salt thereof and a pharmaceutically acceptable carrier.

5. A method for antagonizing the 5-$HT_{2B}$ receptor and the 5-$HT_7$ receptor, which comprises administering to a patient the compound described in claim 1 or a pharmaceutically acceptable salt thereof.

6. A method for treating irritable bowel syndrome, which comprises administering a therapeutically effective amount of the compound described in claim 1 or a pharmaceutically acceptable salt thereof to a patient.

7. The compound described in claim 2, wherein $R^1$ is —N═C($NH_2$)$_2$, —N($R^0$)-(nitrogen-containing saturated heterocyclic group which has a linkage on a carbon atom as the ring atom and may be substituted with lower alkyl), or —N($R^0$)-lower alkylene-(nitrogen-containing saturated heterocyclic group which may be substituted with lower alkyl).

8. The compound described in claim 7, wherein $R^1$ is —N═C($NH_2$)$_2$, —NH-(nitrogen-containing saturated heterocyclic group which has a linkage on a carbon atom as the ring atom and may be substituted with lower alkyl) or —NH-lower alkylene-(nitrogen-containing saturated heterocyclic group which may be substituted with lower alkyl).

9. The compound described in claim 8, wherein $R^1$ is —NH-(nitrogen-containing saturated heterocyclic group which has a linkage on a carbon atom as the ring atom and may be substituted with lower alkyl).

10. The compound described in claim 1, wherein $R^5$ is —H.

11. The compound described in claim 3, which is 5-tert-butyl-1-[2-(4-fluorophenyl)ethyl]-2-methyl-N-[(3S)-1-methylpyrrolidin-3-yl]-1H-pyrrole-3-carboxamide, or a pharmaceutically acceptable salt thereof.

12. The compound described in claim 3, which is 5-tert-butyl-1-[2-(4-fluorophenyl)ethyl]-2-methyl-N-[(3R)-1-methylpyrrolidin-3-yl]-1H-pyrrole-3-carboxamide, or a pharmaceutically acceptable salt thereof.

13. The compound described in claim 3, which is 5-tert-butyl-1-[2-(4-fluorophenyl)ethyl]-2-methyl-N-{[(2R)-1-methylpyrrolidin-2-yl]methyl}-1H-pyrrole-3-carboxamide, or a pharmaceutically acceptable salt thereof.

14. The compound described in claim 3, which is 5-tert-butyl-1-[2-(4-fluorophenyl)ethyl]-2-methyl-N-{[(2S)-1-methylpyrrolidin-2-yl]methyl}-1H-pyrrole-3-carboxamide, or a pharmaceutically acceptable salt thereof.

* * * * *

UNITED STATES PATENT AND TRADEMARK OFFICE

CERTIFICATE OF CORRECTION

PATENT NO. : 8,222,274 B2
APPLICATION NO. : 12/278609
DATED : July 17, 2012
INVENTOR(S) : Ryushi Seo et al.

It is certified that error appears in the above-identified patent and that said Letters Patent is hereby corrected as shown below:

COLUMN 1:

Line 26, “this is deeply concerned” should read --is involved--; and
Line 56, “to public” should be deleted.

COLUMN 4:

Line 59, “has” should read --have--.

COLUMN 6:

Line 53, “faces” should read --feces--;
Line 59, “faces” should read --feces--; and
Line 65, “faces” should read --feces--.

COLUMN 7:

Line 5, “faces” should read --feces--;
Line 11, “faces” should read --feces--;
Line 17, “faces” should read --feces--; and
Line 64, “ethyl,” should read --ethyl;--.

COLUMN 21:

Line 13, “lizes,” should read --lizers,--.

Signed and Sealed this
Twentieth Day of November, 2012

David J. Kappos
*Director of the United States Patent and Trademark Office*

COLUMN 24:

Line 12, “faces” should read --feces--; and
Line 24, “faces” should read --feces--.

COLUMN 25:

Line 13, “$(M^{-1}$-1” should read --$(M^{-}$-1--.

COLUMN 28:

Line 52, “rising” should read --raising--; and
Line 64, “a” should read --an--.

COLUMN 32:

Line 59, “a” should read --an--.

COLUMN 62:

Line 5, “$-(CH_2)_2)$” should read -- $–(CH_2)_2$--.